(12) United States Patent
Podhajsky (10) Patent No.: US 7,846,158 B2
(45) Date of Patent: Dec. 7, 2010

(54) APPARATUS AND METHOD FOR ELECTRODE THERMOSURGERY (75) Inventor: Ronald J. Podhajsky, Boulder, CO (US)

(73) Assignee: Covidien AG, Neuhausen am Rheinfall (CH)

( * ) Notice: Subject to any disclaimer, the term of this patent is extended or adjusted under 35 U.S.C. 154(b) by 1074 days.

(21) Appl. No.: 11/418,880

(22) Filed: May 5, 2006

(65) Prior Publication Data
US 2007/0260235 A1 Nov. 8, 2007

(51) Int. Cl.
A61B 18/18 (2006.01)
(52) U.S. Cl. .......................... 606/41; 606/49
(58) Field of Classification Search ............. 606/27–31, 606/41–42, 45
See application file for complete search history.

(56) References Cited

U.S. PATENT DOCUMENTS

| 371,664 | A | 10/1887 | Brannan et al. |
| 702,472 | A | 6/1902 | Pignolet |
| 728,883 | A | 5/1903 | Downes |
| 1,586,645 | A | 6/1926 | Bierman |
| 1,813,902 | A | 7/1931 | Bovie |
| 2,002,594 | A | 5/1935 | Wappler et al. |
| 2,011,169 | A | 8/1935 | Wappler |
| 2,031,682 | A | 2/1936 | Wappler et al. |
| 2,176,479 | A | 10/1939 | Willis |
| 2,279,753 | A | 4/1942 | Knopp |
| 2,305,156 | A | 12/1942 | Grubel |
| 2,632,661 | A | 3/1953 | Cristofv |
| 2,668,538 | A | 2/1954 | Baker |
| 2,796,065 | A | 6/1957 | Kapp |
| 3,459,187 | A | 8/1969 | Pallotta |
| 3,643,663 | A | 2/1972 | Sutter |
| 3,651,811 | A | 3/1972 | Hildebrandt et al. |
| 3,720,896 | A | 3/1973 | Beierlein |

(Continued)

FOREIGN PATENT DOCUMENTS

CA 2104423 2/1994

(Continued)

OTHER PUBLICATIONS

Int'l Search Report EP 05016399 dated Jan. 5, 2006.

(Continued)

Primary Examiner—Thomas J Sweet
Assistant Examiner—Samantha Good (57) ABSTRACT

An electrosurgical instrument for use with a source of electrical energy to ablate tissue in a living subject is provided. The instrument includes an elongated tissue-penetrating electrode including a rigid tubular member having a closed distal end defining an interior cavity extending from the closed distal end to a proximal end of the rigid tubular member. The rigid tubular member defines an electrically conductive surface capable of receiving electrical energy from the source of electrical energy. The instrument further includes at least one electrically conductive segment located on the electrode, the segment being configured to receive locally controlled electrosurgical energy from the rigid tubular member. An insulation layer is disposed upon the elongated tissue-penetrating electrode. The layer defines an exposed portion of the electrode at the distal end. The instrument also includes at least one sensor that detects a temperature during ablation and at least one transistor that connects the rigid tubular member with the at least one electrically conductive segment.

20 Claims, 6 Drawing Sheets

U.S. PATENT DOCUMENTS

| | | | |
|---|---|---|---|
| 3,862,630 A | 1/1975 | Balamuth | |
| 3,863,339 A | 2/1975 | Reaney et al. | |
| 3,866,610 A | 2/1975 | Kletschka | |
| 3,911,766 A | 10/1975 | Fridolph et al. | |
| 3,920,021 A | 11/1975 | Hiltebrandt | |
| 3,921,641 A | 11/1975 | Hulka | |
| 3,938,527 A | 2/1976 | Rioux et al. | |
| 3,952,749 A | 4/1976 | Fridolph et al. | |
| 3,970,088 A | 7/1976 | Morrison | |
| 3,987,795 A | 10/1976 | Morrison | |
| 4,005,714 A | 2/1977 | Hiltebrandt | |
| 4,041,952 A | 8/1977 | Morrison, Jr. et al. | |
| 4,043,342 A | 8/1977 | Morrison, Jr. | |
| 4,074,718 A | 2/1978 | Morrison, Jr. | |
| 4,088,134 A | 5/1978 | Mazzariello | |
| 4,112,950 A | 9/1978 | Pike | |
| 4,127,222 A | 11/1978 | Adams | |
| 4,128,099 A | 12/1978 | Bauer | |
| 4,165,746 A | 8/1979 | Burgin | |
| 4,233,734 A | 11/1980 | Bies | |
| 4,300,564 A | 11/1981 | Furihata | |
| D263,020 S | 2/1982 | Rau, III | |
| 4,370,980 A | 2/1983 | Lottick | |
| 4,375,218 A | 3/1983 | DiGeronimo | |
| 4,416,276 A | 11/1983 | Newton et al. | |
| 4,418,692 A | 12/1983 | Guay | |
| 4,452,246 A | 6/1984 | Bader et al. | |
| 4,492,231 A | 1/1985 | Auth | |
| 4,552,143 A | 11/1985 | Lottick | |
| 4,574,804 A | 3/1986 | Kurwa | |
| 4,597,379 A | 7/1986 | Kihn et al. | |
| 4,600,007 A | 7/1986 | Lahodny et al. | |
| 4,655,215 A | 4/1987 | Pike | |
| 4,655,216 A | 4/1987 | Tischer | |
| 4,657,016 A | 4/1987 | Garito et al. | |
| 4,662,372 A | 5/1987 | Sharkany et al. | |
| 4,671,274 A | 6/1987 | Sorochenko | |
| 4,685,459 A | 8/1987 | Xoch et al. | |
| D295,893 S | 5/1988 | Sharkany et al. | |
| D295,894 S | 5/1988 | Sharkany et al. | |
| 4,754,892 A | 7/1988 | Retief | |
| 4,763,669 A | 8/1988 | Jaeger | |
| 4,827,929 A | 5/1989 | Hodge | |
| 4,846,171 A | 7/1989 | Kauphusman et al. | |
| 4,887,612 A | 12/1989 | Esser et al. | |
| 4,938,761 A | 7/1990 | Ensslin | |
| 4,985,030 A | 1/1991 | Melzer et al. | |
| 5,007,908 A | 4/1991 | Rydell | |
| 5,026,370 A | 6/1991 | Lottick | |
| 5,035,695 A | 7/1991 | Weber, Jr. et al. | |
| 5,084,057 A | 1/1992 | Green et al. | |
| 5,099,840 A | 3/1992 | Goble et al. | |
| 5,116,332 A | 5/1992 | Lottick | |
| 5,147,357 A | 9/1992 | Rose et al. | |
| 5,151,102 A | 9/1992 | Xamiyama et al. | |
| 5,176,695 A | 1/1993 | Dulebohn | |
| 5,190,541 A | 3/1993 | Abele et al. | |
| 5,196,009 A | 3/1993 | Kirwan, Jr. | |
| 5,197,964 A | 3/1993 | Parins | |
| 5,215,101 A | 6/1993 | Jacobs et al. | |
| 5,217,457 A | 6/1993 | Delahuerga et al. | |
| 5,217,458 A | 6/1993 | Parins | |
| 5,217,460 A | 6/1993 | Knoepfler | |
| 5,219,354 A | 6/1993 | Choudhury et al. | |
| 5,244,462 A | 9/1993 | Delahuerga et al. | |
| 5,250,047 A | 10/1993 | Rydell | |
| 5,250,063 A | 10/1993 | Abidin et al. | |
| 5,258,001 A | 11/1993 | Corman | |
| 5,258,006 A | 11/1993 | Rydell et al. | |
| 5,261,918 A | 11/1993 | Phillips et al. | |
| 5,275,615 A | 1/1994 | Rose | |
| 5,277,201 A | 1/1994 | Stern | |
| 5,282,799 A | 2/1994 | Rydell | |
| 5,290,286 A | 3/1994 | Parins | |
| 5,304,203 A | 4/1994 | El-Mallawany et al. | |
| 5,308,357 A | 5/1994 | Lichtman | |
| 5,314,445 A | 5/1994 | Degwitz et al. | |
| 5,318,589 A | 6/1994 | Lichtman | |
| 5,324,289 A | 6/1994 | Eggers | |
| 5,326,806 A | 7/1994 | Yokoshima et al. | |
| 5,330,471 A | 7/1994 | Eggers | |
| 5,334,183 A | 8/1994 | Wuchinich | |
| 5,334,215 A | 8/1994 | Chen | |
| 5,336,220 A | 8/1994 | Ryan et al. | |
| 5,336,221 A | 8/1994 | Anderson | |
| 5,342,359 A | 8/1994 | Rydell | |
| 5,342,381 A | 8/1994 | Tidemand | |
| 5,342,393 A | 8/1994 | Stack | |
| 5,344,424 A | 9/1994 | Roberts et al. | |
| 5,352,222 A | 10/1994 | Rydell | |
| 5,354,271 A | 10/1994 | Voda | |
| 5,356,408 A | 10/1994 | Rydell | |
| 5,366,477 A | 11/1994 | LeMarie, III et al. | |
| 5,368,600 A | 11/1994 | Failla et al. | |
| 5,376,089 A | 12/1994 | Smith | |
| 5,383,897 A | 1/1995 | Wholey | |
| 5,389,098 A | 2/1995 | Tsuruta et al. | |
| 5,389,104 A | 2/1995 | Hahnen et al. | |
| 5,391,166 A | 2/1995 | Eggers | |
| 5,391,183 A | 2/1995 | Janzen et al. | |
| 5,396,900 A | 3/1995 | Slater et al. | |
| 5,403,312 A | 4/1995 | Yates et al. | |
| 5,411,519 A | 5/1995 | Tovey et al. | |
| 5,411,520 A | 5/1995 | Nash et al. | |
| 5,413,571 A | 5/1995 | Katsaros et al. | |
| 5,415,657 A | 5/1995 | Taymor-Luria | |
| 5,422,567 A | 6/1995 | Matsunaga | |
| 5,423,810 A | 6/1995 | Goble et al. | |
| 5,425,690 A | 6/1995 | Chang | |
| 5,425,739 A | 6/1995 | Jessen | |
| 5,429,616 A | 7/1995 | Schaffer | |
| 5,431,672 A | 7/1995 | Cote et al. | |
| 5,431,674 A | 7/1995 | Basile et al. | |
| 5,437,292 A | 8/1995 | Kipshidze et al. | |
| 5,438,302 A | 8/1995 | Goble | |
| 5,441,517 A | 8/1995 | Kensey et al. | |
| 5,443,463 A | 8/1995 | Stern et al. | |
| 5,443,464 A | 8/1995 | Russell et al. | |
| 5,443,480 A | 8/1995 | Jacobs et al. | |
| 5,445,638 A | 8/1995 | Rydell et al. | |
| 5,445,658 A | 8/1995 | Durrfeld et al. | |
| 5,451,224 A | 9/1995 | Goble et al. | |
| 5,456,684 A | 10/1995 | Schmidt et al. | |
| 5,458,598 A | 10/1995 | Feinberg et al. | |
| 5,460,629 A | 10/1995 | Shlain et al. | |
| 5,462,546 A | 10/1995 | Rydell | |
| 5,472,443 A | 12/1995 | Cordis et al. | |
| 5,478,351 A | 12/1995 | Meade et al. | |
| 5,480,409 A | 1/1996 | Riza | |
| 5,484,436 A | 1/1996 | Eggers et al. | |
| 5,496,312 A | 3/1996 | Klicek | |
| 5,496,317 A | 3/1996 | Goble et al. | |
| 5,496,347 A | 3/1996 | Hashiguchi et al. | |
| 5,499,997 A | 3/1996 | Sharpe et al. | |
| 5,509,922 A | 4/1996 | Aranyi et al. | |
| 5,514,134 A | 5/1996 | Rydell et al. | |
| 5,527,313 A | 6/1996 | Scott et al. | |
| 5,531,744 A | 7/1996 | Nardella et al. | |
| 5,536,251 A | 7/1996 | Evard et al. | |
| 5,540,684 A | 7/1996 | Hassler, Jr. | |
| 5,540,685 A | 7/1996 | Parins et al. | |
| 5,540,715 A | 7/1996 | Katsaros et al. | |
| 5,542,945 A | 8/1996 | Fritzsch | |
| 5,558,671 A | 9/1996 | Yates | |

| | | | | | | |
|---|---|---|---|---|---|---|
| 5,558,672 | A | 9/1996 | Edwards et al. | 5,827,271 | A | 10/1998 | Buysse et al. |
| 5,562,699 | A | 10/1996 | Heimberger et al. | 5,827,279 | A | 10/1998 | Hughett et al. |
| 5,569,241 | A | 10/1996 | Edwards | 5,827,281 | A | 10/1998 | Levin |
| 5,569,243 | A | 10/1996 | Kortenbach et al. | 5,827,323 | A | 10/1998 | Klieman et al. |
| 5,571,100 | A | 11/1996 | Goble et al. | 5,827,548 | A | 10/1998 | Lavallee et al. |
| 5,573,424 | A | 11/1996 | Poppe | 5,833,690 | A | 11/1998 | Yates et al. |
| 5,573,534 | A | 11/1996 | Stone | 5,843,075 | A * | 12/1998 | Taylor ............... 606/34 |
| 5,573,535 | A | 11/1996 | Viklund | 5,843,080 | A | 12/1998 | Fleenor et al. |
| 5,575,805 | A | 11/1996 | Li | 5,849,022 | A | 12/1998 | Sakashita et al. |
| 5,578,052 | A | 11/1996 | Koros et al. | 5,853,412 | A | 12/1998 | Mayenberger |
| 5,582,611 | A | 12/1996 | Tsuruta et al. | 5,860,976 | A | 1/1999 | Billings et al. |
| 5,585,896 | A | 12/1996 | Yamazaki et al. | 5,876,401 | A | 3/1999 | Schulze et al. |
| 5,590,570 | A | 1/1997 | LeMaire, III et al. | 5,882,567 | A | 3/1999 | Cavallaro et al. |
| 5,601,601 | A | 2/1997 | Tal et al. | 5,891,141 | A | 4/1999 | Rydell |
| 5,603,711 | A | 2/1997 | Parins et al. | 5,891,142 | A | 4/1999 | Eggers et al. |
| 5,603,723 | A | 2/1997 | Aranyi et al. | 5,893,863 | A | 4/1999 | Yoon |
| 5,611,798 | A | 3/1997 | Eggers | 5,893,875 | A | 4/1999 | O'Connor et al. |
| 5,620,453 | A | 4/1997 | Nallakrishnan | 5,893,877 | A | 4/1999 | Gampp, Jr. et al. |
| 5,624,452 | A | 4/1997 | Yates | 5,902,301 | A | 5/1999 | Olig |
| 5,626,578 | A | 5/1997 | Tihon | 5,906,630 | A | 5/1999 | Anderhub et al. |
| 5,626,609 | A | 5/1997 | Zvenyatsky et al. | 5,908,420 | A | 6/1999 | Parins et al. |
| 5,630,833 | A | 5/1997 | Katsaros et al. | 5,908,432 | A | 6/1999 | Pan |
| 5,637,110 | A | 6/1997 | Pennybacker et al. | 5,911,719 | A | 6/1999 | Eggers |
| 5,638,003 | A | 6/1997 | Hall | 5,913,874 | A | 6/1999 | Berns et al. |
| 5,643,294 | A | 7/1997 | Tovey et al. | 5,921,984 | A | 7/1999 | Sutcu et al. |
| 5,647,869 | A | 7/1997 | Goble et al. | 5,925,043 | A | 7/1999 | Kumar et al. |
| 5,647,871 | A | 7/1997 | Levine et al. | 5,935,126 | A | 8/1999 | Riza |
| 5,649,959 | A | 7/1997 | Hannam et al. | 5,944,718 | A | 8/1999 | Austin et al. |
| 5,658,281 | A | 8/1997 | Heard | 5,951,549 | A | 9/1999 | Richardson et al. |
| 5,662,667 | A | 9/1997 | Knodel | 5,954,720 | A | 9/1999 | Wilson et al. |
| 5,665,100 | A | 9/1997 | Yoon | 5,957,923 | A | 9/1999 | Hahnen et al. |
| 5,667,526 | A | 9/1997 | Levin | 5,960,544 | A | 10/1999 | Beyers |
| 5,674,220 | A | 10/1997 | Fox et al. | 5,961,514 | A | 10/1999 | Long et al. |
| 5,681,282 | A | 10/1997 | Eggers et al. | 5,964,758 | A | 10/1999 | Dresden |
| 5,688,270 | A | 11/1997 | Yates et al. | 5,976,132 | A | 11/1999 | Morris |
| 5,693,051 | A | 12/1997 | Schulze et al. | 5,984,939 | A | 11/1999 | Yoon |
| 5,695,522 | A | 12/1997 | LeMaire, III et al. | 5,989,277 | A | 11/1999 | LeMaire, III et al. |
| 5,700,261 | A | 12/1997 | Brinkerhoff | 5,997,565 | A | 12/1999 | Inoue |
| 5,702,390 | A | 12/1997 | Austin et al. | 6,004,335 | A | 12/1999 | Vaitekunas et al. |
| 5,707,369 | A | 1/1998 | Vaitekunas et al. | 6,010,516 | A | 1/2000 | Hulka et al. |
| 5,709,680 | A | 1/1998 | Yates et al. | 6,024,741 | A | 2/2000 | Williamson et al. |
| 5,716,366 | A | 2/1998 | Yates | 6,024,744 | A | 2/2000 | Kese et al. |
| 5,720,744 | A | 2/1998 | Eggleston et al. | 6,030,384 | A | 2/2000 | Nezhat |
| 5,722,421 | A | 3/1998 | Francese et al. | 6,033,399 | A | 3/2000 | Gines |
| 5,725,536 | A | 3/1998 | Oberlin et al. | 6,039,733 | A | 3/2000 | Buysse et al. |
| 5,727,428 | A | 3/1998 | LeMaire, III et al. | 6,041,679 | A | 3/2000 | Slater et al. |
| 5,735,848 | A | 4/1998 | Yates et al. | 6,050,996 | A | 4/2000 | Schmaltz et al. |
| 5,743,906 | A | 4/1998 | Parins et al. | 6,053,914 | A | 4/2000 | Eggers et al. |
| 5,755,717 | A | 5/1998 | Yates et al. | 6,053,933 | A | 4/2000 | Balazs et al. |
| 5,766,130 | A | 6/1998 | Selmonosky | D424,694 | S | 5/2000 | Tetzlaff et al. |
| 5,766,166 | A | 6/1998 | Hooven | D425,201 | S | 5/2000 | Tetzlaff et al. |
| 5,766,170 | A | 6/1998 | Eggers | 6,059,782 | A | 5/2000 | Novak et al. |
| 5,769,849 | A | 6/1998 | Eggers | 6,074,386 | A | 6/2000 | Goble et al. |
| 5,772,655 | A | 6/1998 | Bauer et al. | RE36,795 | E | 7/2000 | Rydell |
| 5,772,670 | A | 6/1998 | Brosa | 6,083,223 | A | 7/2000 | Baker |
| 5,776,128 | A | 7/1998 | Eggers | 6,086,586 | A | 7/2000 | Hooven |
| 5,776,130 | A | 7/1998 | Buysse et al. | 6,090,107 | A | 7/2000 | Borgmeier et al. |
| 5,779,701 | A | 7/1998 | McBrayer et al. | 6,096,037 | A | 8/2000 | Mulier et al. |
| H1745 | H | 8/1998 | Paraschac | 6,099,550 | A | 8/2000 | Yoon |
| 5,792,137 | A | 8/1998 | Carr et al. | 6,102,909 | A | 8/2000 | Chen et al. |
| 5,792,177 | A | 8/1998 | Kaseda | 6,110,171 | A | 8/2000 | Rydell |
| 5,797,927 | A | 8/1998 | Yoon | 6,113,596 | A | 9/2000 | Hooven et al. |
| 5,797,938 | A | 8/1998 | Paraschac et al. | 6,113,598 | A | 9/2000 | Baker |
| 5,797,941 | A | 8/1998 | Schulze et al. | 6,117,158 | A | 9/2000 | Measamer et al. |
| 5,797,958 | A | 8/1998 | Yoon | 6,123,701 | A | 9/2000 | Nezhat |
| 5,800,449 | A | 9/1998 | Wales | H1904 | H | 10/2000 | Yates et al. |
| 5,807,393 | A | 9/1998 | Williamson, IV et al. | 6,126,658 | A | 10/2000 | Baker |
| 5,810,808 | A | 9/1998 | Eggers | 6,152,923 | A | 11/2000 | Ryan |
| 5,810,811 | A | 9/1998 | Yates et al. | 6,162,220 | A | 12/2000 | Nezhat |
| 5,810,877 | A | 9/1998 | Roth et al. | 6,174,309 | B1 | 1/2001 | Wrublewski et al. |
| 5,814,043 | A | 9/1998 | Shapeton | 6,179,834 | B1 | 1/2001 | Buysse et al. |
| 5,817,093 | A | 10/1998 | Williamson, IV et al. | 6,179,837 | B1 | 1/2001 | Hooven |
| 5,820,630 | A | 10/1998 | Lind | 6,183,467 | B1 | 2/2001 | Shapeton et al. |

| | | |
|---|---|---|
| 6,187,003 B1 | 2/2001 | Buysse et al. |
| 6,190,386 B1 | 2/2001 | Rydell |
| 6,193,718 B1 | 2/2001 | Kortenbach et al. |
| 6,206,876 B1 | 3/2001 | Levine et al. |
| 6,206,877 B1 | 3/2001 | Kese et al. |
| 6,217,602 B1 | 4/2001 | Redmon |
| 6,221,039 B1 | 4/2001 | Durgin et al. |
| 6,224,593 B1 | 5/2001 | Ryan et al. |
| 6,228,080 B1 | 5/2001 | Gines |
| 6,228,083 B1 | 5/2001 | Lands et al. |
| 6,267,761 B1 | 7/2001 | Ryan |
| 6,270,497 B1 | 8/2001 | Sekino et al. |
| 6,270,508 B1 | 8/2001 | Klieman et al. |
| 6,273,887 B1 | 8/2001 | Yamauchi et al. |
| 6,277,117 B1 | 8/2001 | Tetzlaff et al. |
| 6,280,458 B1 | 8/2001 | Boche et al. |
| 6,283,961 B1 | 9/2001 | Underwood et al. |
| D449,886 S | 10/2001 | Tetzlaff et al. |
| 6,302,424 B1 | 10/2001 | Gisinger et al. |
| 6,319,451 B1 | 11/2001 | Brune |
| 6,322,561 B1 | 11/2001 | Eggers et al. |
| 6,334,860 B1 | 1/2002 | Dorn |
| 6,334,861 B1 | 1/2002 | Chandler et al. |
| 6,345,532 B1 | 2/2002 | Coudray et al. |
| 6,350,264 B1 | 2/2002 | Hooven |
| 6,352,536 B1 | 3/2002 | Buysse et al. |
| 6,358,249 B1 | 3/2002 | Chen et al. |
| 6,358,268 B1 | 3/2002 | Hunt et al. |
| D457,958 S | 5/2002 | Dycus et al. |
| D457,959 S | 5/2002 | Tetzlaff et al. |
| 6,387,094 B1 | 5/2002 | Eitenmuller |
| 6,391,035 B1 | 5/2002 | Appleby et al. |
| 6,398,779 B1 | 6/2002 | Buysse et al. |
| 6,402,747 B1 | 6/2002 | Lindemann et al. |
| 6,409,728 B1 | 6/2002 | Ehr et al. |
| H2037 H | 7/2002 | Yates et al. |
| 6,419,675 B1 | 7/2002 | Gallo, Sr. |
| 6,421,567 B1 * | 7/2002 | Witte .................... 607/122 |
| 6,425,896 B1 | 7/2002 | Baltschun et al. |
| 6,440,144 B1 | 8/2002 | Bacher |
| 6,443,952 B1 | 9/2002 | Mulier et al. |
| 6,443,970 B1 | 9/2002 | Schulze et al. |
| 6,451,018 B1 | 9/2002 | Lands et al. |
| 6,458,125 B1 | 10/2002 | Cosmescu |
| 6,458,128 B1 | 10/2002 | Schulze |
| 6,458,130 B1 | 10/2002 | Frazier et al. |
| 6,464,701 B1 | 10/2002 | Hooven et al. |
| 6,464,702 B2 | 10/2002 | Schulze et al. |
| 6,464,704 B2 | 10/2002 | Schmaltz et al. |
| 6,500,176 B1 | 12/2002 | Truckai et al. |
| 6,506,189 B1 * | 1/2003 | Rittman et al. ............. 606/41 |
| 6,511,480 B1 | 1/2003 | Tetzlaff et al. |
| 6,514,252 B2 | 2/2003 | Nezhat et al. |
| 6,527,771 B1 | 3/2003 | Weadock et al. |
| 6,558,385 B1 | 5/2003 | McClurken et al. |
| 6,562,037 B2 | 5/2003 | Paton et al. |
| 6,575,969 B1 | 6/2003 | Rittman, III et al. |
| 6,585,735 B1 | 7/2003 | Lands et al. |
| 6,602,252 B2 | 8/2003 | Mollenauer |
| 6,616,658 B2 | 9/2003 | Ineson |
| 6,616,661 B2 | 9/2003 | Wellman et al. |
| 6,620,161 B2 | 9/2003 | Schulze et al. |
| 6,626,901 B1 | 9/2003 | Treat et al. |
| 6,641,595 B1 | 11/2003 | Moran et al. |
| 6,652,514 B2 | 11/2003 | Ellman et al. |
| 6,652,521 B2 | 11/2003 | Schulze |
| 6,656,177 B2 | 12/2003 | Truckai et al. |
| 6,660,072 B2 | 12/2003 | Chatterjee |
| 6,669,696 B2 | 12/2003 | Bacher et al. |
| 6,676,660 B2 | 1/2004 | Wampler et al. |
| 6,679,882 B1 | 1/2004 | Kornerup |
| 6,682,527 B2 | 1/2004 | Strul |
| 6,682,528 B2 | 1/2004 | Frazier et al. |
| 6,685,724 B1 | 2/2004 | Haluck |
| 6,689,131 B2 | 2/2004 | McClurken |
| 6,692,445 B2 | 2/2004 | Roberts et al. |
| 6,695,840 B2 | 2/2004 | Schulze |
| 6,702,810 B2 | 3/2004 | McClurken et al. |
| 6,726,068 B2 | 4/2004 | Miller |
| 6,726,686 B2 | 4/2004 | Buysse et al. |
| 6,733,498 B2 | 5/2004 | Paton et al. |
| 6,736,813 B2 | 5/2004 | Yamauchi et al. |
| 6,743,229 B2 | 6/2004 | Buysse et al. |
| 6,743,230 B2 | 6/2004 | Lutze et al. |
| 6,757,977 B2 | 7/2004 | Dambal et al. |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,775,575 B2 | 8/2004 | Bommannan et al. |
| 6,776,780 B2 | 8/2004 | Mulier et al. |
| 6,790,217 B2 | 9/2004 | Schulze et al. |
| 6,796,981 B2 | 9/2004 | Wham et al. |
| D496,997 S | 10/2004 | Dycus et al. |
| 6,802,843 B2 | 10/2004 | Truckai et al. |
| 6,808,525 B2 | 10/2004 | Latterell et al. |
| D499,181 S | 11/2004 | Dycus et al. |
| 6,818,000 B2 | 11/2004 | Muller et al. |
| 6,860,880 B2 | 3/2005 | Treat et al. |
| 6,887,240 B1 | 5/2005 | Lands et al. |
| 6,926,716 B2 | 8/2005 | Baker et al. |
| 6,929,644 B2 | 8/2005 | Truckai et al. |
| 6,932,810 B2 | 8/2005 | Ryan |
| 6,932,816 B2 | 8/2005 | Phan |
| 6,934,134 B2 | 8/2005 | Mori et al. |
| 6,936,061 B2 | 8/2005 | Sasaki |
| 6,942,662 B2 | 9/2005 | Goble et al. |
| 6,953,461 B2 | 10/2005 | McClurken et al. |
| 6,958,070 B2 | 10/2005 | Witt et al. |
| 6,960,210 B2 | 11/2005 | Lands et al. |
| 6,964,662 B2 | 11/2005 | Kidooka |
| 6,966,907 B2 | 11/2005 | Goble |
| 6,977,495 B2 | 12/2005 | Donofrio |
| 6,979,786 B2 | 12/2005 | Aukland et al. |
| 6,994,707 B2 | 2/2006 | Ellman et al. |
| 6,994,709 B2 | 2/2006 | Iida |
| 7,011,657 B2 | 3/2006 | Truckai et al. |
| 7,033,354 B2 | 4/2006 | Keppel |
| 7,033,356 B2 | 4/2006 | Latterell et al. |
| 7,041,102 B2 | 5/2006 | Truckai et al. |
| 7,044,948 B2 | 5/2006 | Keppel |
| 7,052,496 B2 | 5/2006 | Yamauchi |
| D525,361 S | 7/2006 | Hushka |
| 7,070,597 B2 | 7/2006 | Truckai et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,090,673 B2 | 8/2006 | Dycus et al. |
| 7,090,689 B2 | 8/2006 | Nagase et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 | 9/2006 | Sartor et al. |
| 7,112,199 B2 | 9/2006 | Cosmescu |
| D531,311 S | 10/2006 | Guerra et al. |
| 7,115,123 B2 | 10/2006 | Knowlton et al. |
| 7,118,570 B2 | 10/2006 | Tetzlaff et al. |
| 7,118,587 B2 | 10/2006 | Dycus et al. |
| 7,131,860 B2 | 11/2006 | Sartor et al. |
| 7,131,970 B2 | 11/2006 | Moses et al. |
| 7,131,971 B2 | 11/2006 | Dycus et al. |
| 7,135,020 B2 | 11/2006 | Lawes et al. |
| D533,942 S | 12/2006 | Kerr et al. |
| 7,145,757 B2 | 12/2006 | Shea et al. |
| 7,147,638 B2 | 12/2006 | Chapman et al. |
| 7,150,097 B2 | 12/2006 | Sremcich et al. |
| 7,150,749 B2 | 12/2006 | Dycus et al. |

| | | | | | | |
|---|---|---|---|---|---|---|
| D535,027 S | 1/2007 | James et al. | | 2004/0236325 A1 | 11/2004 | Tetzlaff et al. |
| 7,156,842 B2 | 1/2007 | Sartor et al. | | 2004/0236326 A1 | 11/2004 | Schulze et al. |
| 7,156,846 B2 | 1/2007 | Dycus et al. | | 2004/0243125 A1 | 12/2004 | Dycus et al. |
| 7,160,298 B2 | 1/2007 | Lawes et al. | | 2004/0249371 A1 | 12/2004 | Dycus et al. |
| 7,160,299 B2 | 1/2007 | Baily | | 2004/0249374 A1 | 12/2004 | Tetzlaff et al. |
| 7,169,146 B2 | 1/2007 | Truckai et al. | | 2004/0249425 A1 * | 12/2004 | Roy et al. ............ 607/99 |
| 7,179,258 B2 | 2/2007 | Buysse et al. | | 2004/0250419 A1 | 12/2004 | Sremcich et al. |
| 7,195,631 B2 | 3/2007 | Dumbauld | | 2004/0254573 A1 | 12/2004 | Dycus et al. |
| D541,418 S | 4/2007 | Schechter et al. | | 2004/0260281 A1 | 12/2004 | Baxter, III et al. |
| 7,207,990 B2 | 4/2007 | Lands et al. | | 2005/0004564 A1 | 1/2005 | Wham et al. |
| D541,938 S | 5/2007 | Kerr et al | | 2005/0004568 A1 | 1/2005 | Lawes et al. |
| 7,223,265 B2 | 5/2007 | Keppel | | 2005/0004570 A1 | 1/2005 | Chapman et al. |
| 7,232,440 B2 | 6/2007 | Dumbauld et al. | | 2005/0021025 A1 | 1/2005 | Buysse et al. |
| 7,241,288 B2 | 7/2007 | Braun | | 2005/0021026 A1 | 1/2005 | Baily |
| 7,241,296 B2 | 7/2007 | Buysse et al. | | 2005/0021027 A1 | 1/2005 | Shields et al. |
| 7,252,667 B2 | 8/2007 | Moses et al. | | 2005/0033278 A1 | 2/2005 | McClurken et al. |
| 7,255,697 B2 | 8/2007 | Dycus et al. | | 2005/0096645 A1 | 5/2005 | Wellman et al. |
| 7,267,677 B2 | 9/2007 | Johnson et al. | | 2005/0101951 A1 | 5/2005 | Wham et al. |
| 7,270,660 B2 | 9/2007 | Ryan | | 2005/0101952 A1 | 5/2005 | Lands et al. |
| 7,270,664 B2 | 9/2007 | Johnson et al. | | 2005/0107784 A1 | 5/2005 | Moses et al. |
| 7,276,068 B2 | 10/2007 | Johnson et al. | | 2005/0107785 A1 | 5/2005 | Dycus et al. |
| 7,300,435 B2 | 11/2007 | Wham et al. | | 2005/0113818 A1 | 5/2005 | Sartor et al. |
| 7,303,557 B2 | 12/2007 | Wham et al. | | 2005/0113819 A1 | 5/2005 | Wham et al. |
| 7,314,471 B2 | 1/2008 | Holman | | 2005/0113826 A1 | 5/2005 | Johnson et al. |
| 7,329,256 B2 | 2/2008 | Johnson et al. | | 2005/0113827 A1 | 5/2005 | Dumbauld et al. |
| 7,329,257 B2 | 2/2008 | Kanehira et al. | | 2005/0113828 A1 | 5/2005 | Shields et al. |
| D564,662 S | 3/2008 | Moses et al. | | 2005/0119655 A1 | 6/2005 | Moses et al. |
| 7,342,754 B2 | 3/2008 | Fitzgerald et al. | | 2005/0149017 A1 | 7/2005 | Dycus |
| 7,344,268 B2 | 3/2008 | Jigamian | | 2005/0149151 A1 | 7/2005 | Orszulak et al. |
| 7,367,976 B2 | 5/2008 | Lawes et al. | | 2005/0187547 A1 | 8/2005 | Sugi |
| 2002/0013583 A1 | 1/2002 | Camran et al. | | 2005/0197659 A1 | 9/2005 | Bahney |
| 2002/0049442 A1 | 4/2002 | Roberts et al. | | 2005/0203504 A1 | 9/2005 | Wham et al. |
| 2002/0099372 A1 | 7/2002 | Schulze et al. | | 2005/0240179 A1 | 10/2005 | Buysse et al. |
| 2002/0107517 A1 | 8/2002 | Witt et al. | | 2006/0052778 A1 | 3/2006 | Chapman et al. |
| 2002/0111624 A1 | 8/2002 | Witt et al. | | 2006/0064085 A1 | 3/2006 | Schechter et al. |
| 2002/0188294 A1 | 12/2002 | Couture et al. | | 2006/0074417 A1 | 4/2006 | Cunningham et al. |
| 2003/0014052 A1 | 1/2003 | Buysse et al. | | 2006/0079888 A1 | 4/2006 | Mulier et al. |
| 2003/0014053 A1 | 1/2003 | Nguyen et al. | | 2006/0079890 A1 | 4/2006 | Guerra |
| 2003/0018331 A1 | 1/2003 | Dycus et al. | | 2006/0079891 A1 | 4/2006 | Arts et al. |
| 2003/0018332 A1 | 1/2003 | Schmaltz et al. | | 2006/0116675 A1 | 6/2006 | McClurken et al. |
| 2003/0032956 A1 | 2/2003 | Lands et al. | | 2006/0129146 A1 | 6/2006 | Dycus et al. |
| 2003/0069571 A1 | 4/2003 | Treat et al. | | 2006/0161150 A1 | 7/2006 | Keppel |
| 2003/0078578 A1 | 4/2003 | Truckai et al. | | 2006/0167450 A1 | 7/2006 | Johnson et al. |
| 2003/0109875 A1 | 6/2003 | Tetzlaff et al. | | 2006/0167452 A1 | 7/2006 | Moses et al. |
| 2003/0114851 A1 | 6/2003 | Truckai et al. | | 2006/0173452 A1 | 8/2006 | Buysse et al. |
| 2003/0139741 A1 | 7/2003 | Goble et al. | | 2006/0189980 A1 | 8/2006 | Johnson et al. |
| 2003/0139742 A1 | 7/2003 | Wampler et al. | | 2006/0189981 A1 | 8/2006 | Dycus et al. |
| 2003/0158549 A1 | 8/2003 | Swanson | | 2006/0190035 A1 | 8/2006 | Hushka et al. |
| 2003/0181910 A1 | 9/2003 | Dycus et al. | | 2006/0217709 A1 | 9/2006 | Couture et al. |
| 2003/0195501 A1 * | 10/2003 | Sherman et al. ............ 606/34 | | 2006/0224158 A1 | 10/2006 | Odom et al. |
| 2003/0199869 A1 | 10/2003 | Johnson et al. | | 2006/0259036 A1 | 11/2006 | Tetzlaf et al. |
| 2003/0216732 A1 | 11/2003 | Truckai et al. | | 2006/0264922 A1 | 11/2006 | Sartor et al. |
| 2003/0220637 A1 | 11/2003 | Truckai et al. | | 2006/0264931 A1 | 11/2006 | Chapman et al. |
| 2003/0229344 A1 | 12/2003 | Dycus et al. | | 2006/0271038 A1 | 11/2006 | Johnson et al. |
| 2004/0030330 A1 | 2/2004 | Brassell et al. | | 2006/0287641 A1 | 12/2006 | Perlin |
| 2004/0030332 A1 | 2/2004 | Knowlton et al. | | 2007/0016182 A1 | 1/2007 | Lipson et al. |
| 2004/0049185 A1 | 3/2004 | Latterell et al. | | 2007/0016187 A1 | 1/2007 | Weinberg et al. |
| 2004/0064151 A1 | 4/2004 | Mollenauer | | 2007/0043352 A1 | 2/2007 | Garrison et al. |
| 2004/0078035 A1 | 4/2004 | Kanehira et al. | | 2007/0043353 A1 | 2/2007 | Dycus et al. |
| 2004/0082952 A1 | 4/2004 | Dycus et al. | | 2007/0055231 A1 | 3/2007 | Dycus et al. |
| 2004/0087943 A1 | 5/2004 | Dycus et al. | | 2007/0060919 A1 | 3/2007 | Isaacson et al. |
| 2004/0115296 A1 | 6/2004 | Duffin | | 2007/0062017 A1 | 3/2007 | Dycus et al. |
| 2004/0116924 A1 | 6/2004 | Dycus et al. | | 2007/0074807 A1 | 4/2007 | Guerra |
| 2004/0116979 A1 | 6/2004 | Truckai et al. | | 2007/0078456 A1 | 4/2007 | Dumbauld et al. |
| 2004/0122423 A1 | 6/2004 | Dycus et al. | | 2007/0078458 A1 | 4/2007 | Dumbauld et al. |
| 2004/0143236 A1 * | 7/2004 | Santini et al. ............ 604/500 | | 2007/0078459 A1 | 4/2007 | Johnson et al. |
| 2004/0143263 A1 | 7/2004 | Schechter et al. | | 2007/0088356 A1 | 4/2007 | Moses et al. |
| 2004/0147925 A1 | 7/2004 | Buysse et al. | | 2007/0106295 A1 | 5/2007 | Garrison et al. |
| 2004/0162557 A1 | 8/2004 | Tetzlaff et al. | | 2007/0106297 A1 | 5/2007 | Dumbauld et al. |
| 2004/0176762 A1 | 9/2004 | Lawes et al. | | 2007/0118111 A1 | 5/2007 | Weinberg |
| 2004/0193153 A1 | 9/2004 | Sarter et al. | | 2007/0118115 A1 | 5/2007 | Artale et al. |
| 2004/0225288 A1 | 11/2004 | Buysse et al. | | 2007/0142833 A1 | 6/2007 | Dycus et al. |
| 2004/0230189 A1 | 11/2004 | Keppel | | 2007/0142834 A1 | 6/2007 | Dumbauld |

| | | | | | | |
|---|---|---|---|---|---|---|
| 2007/0156139 A1 | 7/2007 | Schechter et al. | EP | 1535581 | A2 | 6/2005 |
| 2007/0156140 A1 | 7/2007 | Baily | EP | 1609430 | A1 | 12/2005 |
| 2007/0173811 A1 | 7/2007 | Couture et al. | EP | 1632192 | A1 | 3/2006 |
| 2007/0173814 A1 | 7/2007 | Hixson et al. | EP | 1645238 | A1 | 4/2006 |
| 2007/0179499 A1 | 8/2007 | Garrison | EP | 1645240 | A2 | 4/2006 |
| 2007/0203485 A1 | 8/2007 | Keppel | EP | 1707143 | A1 | 10/2006 |
| 2007/0213706 A1 | 9/2007 | Dumbauld et al. | GB | 2214430 | A | 6/1989 |
| 2007/0213707 A1 | 9/2007 | Dumbauld et al. | GB | 2213416 | | 8/1989 |
| 2007/0213708 A1 | 9/2007 | Dumbauld et al. | JP | 501068 | | 9/1984 |
| 2007/0213712 A1 | 9/2007 | Buysse et al. | JP | 502328 | | 3/1992 |
| 2007/0255279 A1 | 11/2007 | Buysse et al. | JP | 5-5106 | | 1/1993 |
| 2007/0260235 A1 | 11/2007 | Podhajsky | JP | 5-40112 | | 2/1993 |
| 2007/0260238 A1 | 11/2007 | Guerra | JP | 06343644 | A2 | 12/1994 |
| 2007/0260241 A1 | 11/2007 | Dalla Betta et al. | JP | 07265328 | A2 | 10/1995 |
| 2007/0260242 A1 | 11/2007 | Dycus et al. | JP | 08056955 | A2 | 3/1996 |
| 2007/0265216 A1 | 11/2007 | Couture et al. | JP | 08252263 | A2 | 10/1996 |
| 2008/0004616 A1 | 1/2008 | Patrick | JP | 09010223 | A2 | 1/1997 |
| 2008/0009860 A1 | 1/2008 | Odom | JP | 11244298 | A2 | 9/1999 |
| 2008/0015575 A1 | 1/2008 | Odom et al. | JP | 2000342599 | A2 | 12/2000 |
| 2008/0021450 A1 | 1/2008 | Couture | JP | 2000350732 | A2 | 12/2000 |
| 2008/0033428 A1 | 2/2008 | Artale et al. | JP | 2001008944 | A2 | 1/2001 |
| 2008/0039835 A1 | 2/2008 | Johnson et al. | JP | 2001029356 | A2 | 2/2001 |
| 2008/0045947 A1 | 2/2008 | Johnson et al. | JP | 2001128990 | A2 | 5/2001 |
| 2008/0058802 A1 | 3/2008 | Couture et al. | SU | 401367 | | 11/1974 |
| 2008/0082100 A1 | 4/2008 | Orton et al. | WO | WO89/00757 | | 1/1989 |
| | | | WO | WO 92/04873 | | 4/1992 |
| | FOREIGN PATENT DOCUMENTS | | WO | WO 92/06642 | | 4/1992 |
| DE | 2415263 | 10/1975 | WO | WO 94/08524 | A | 4/1994 |
| DE | 2627679 | 1/1977 | WO | WO94/20025 | | 9/1994 |
| DE | 8712328 | 3/1988 | WO | WO 95/02369 | | 1/1995 |
| DE | 4303882 | 8/1994 | WO | WO95/07662 | | 3/1995 |
| DE | 29616210 | 1/1997 | WO | WO 95/07662 | | 3/1995 |
| DE | 19608716 | 4/1997 | WO | WO95/15124 | | 6/1995 |
| DE | 19751106 | 5/1998 | WO | WO96/05776 | | 2/1996 |
| DE | 19751108 | 5/1999 | WO | WO 96/022056 | | 7/1996 |
| EP | 0364216 A1 | 4/1990 | WO | WO 96/13218 | | 9/1996 |
| EP | 0518230 A1 | 12/1992 | WO | WO 97/00646 | | 1/1997 |
| EP | 0 541 930 B1 | 5/1993 | WO | WO 97/00647 | | 1/1997 |
| EP | 0572131 | 12/1993 | WO | WO97/10764 | | 3/1997 |
| EP | 0584787 A1 | 3/1994 | WO | WO 97/10764 | | 3/1997 |
| EP | 0589453 A2 | 3/1994 | WO | WO 97/24073 | | 7/1997 |
| EP | 0623316 A1 | 11/1994 | WO | WO 97/24993 | | 7/1997 |
| EP | 0624348 A2 | 11/1994 | WO | WO 98/27880 | | 7/1998 |
| EP | 0650701 A1 | 5/1995 | WO | WO 99/03407 | | 1/1999 |
| EP | 0694290 A3 | 3/1996 | WO | WO 99/03408 | | 1/1999 |
| EP | 0717966 A1 | 6/1996 | WO | WO 99/03409 | | 1/1999 |
| EP | 0754437 A3 | 3/1997 | WO | WO 99/12488 | | 3/1999 |
| EP | 0853922 A1 | 7/1998 | WO | WO 99/40857 | | 8/1999 |
| EP | 0875209 A1 | 11/1998 | WO | WO 99/40861 | | 8/1999 |
| EP | 0878169 A1 | 11/1998 | WO | WO 99/51158 | | 10/1999 |
| EP | 0887046 A3 | 1/1999 | WO | WO 99/66850 | A | 12/1999 |
| EP | 0923907 A1 | 6/1999 | WO | WO 00/24330 | | 5/2000 |
| EP | 0986990 A1 | 3/2000 | WO | WO00/24331 | | 5/2000 |
| EP | 1034747 A1 | 9/2000 | WO | WO 00/24331 | | 5/2000 |
| EP | 1034748 A1 | 9/2000 | WO | WO 00/41638 | | 7/2000 |
| EP | 1025807 A3 | 10/2000 | WO | WO00/47124 | | 8/2000 |
| EP | 1034746 A3 | 10/2000 | WO | WO 00/53112 | | 9/2000 |
| EP | 1050278 A1 | 11/2000 | WO | WO 01/17448 | A | 3/2001 |
| EP | 1053719 A1 | 11/2000 | WO | WO 01/54604 | | 8/2001 |
| EP | 1053720 A1 | 11/2000 | WO | WO02/07627 | | 1/2002 |
| EP | 1055399 A1 | 11/2000 | WO | WO 02/07627 | | 1/2002 |
| EP | 1055400 A1 | 11/2000 | WO | WO 02/067798 A1 | | 9/2002 |
| EP | 1080694 A1 | 3/2001 | WO | WO 02/080783 | | 10/2002 |
| EP | 1082944 A1 | 3/2001 | WO | WO02/080783 | | 10/2002 |
| EP | 1159926 A2 | 12/2001 | WO | WO 02/080784 | | 10/2002 |
| EP | 1301135 A | 4/2003 | WO | WO02/080784 | | 10/2002 |
| EP | 1330991 A1 | 7/2003 | WO | WO02/080785 | | 10/2002 |
| EP | 1486177 A2 | 6/2004 | WO | WO 02/080785 | | 10/2002 |
| EP | 1472984 A1 | 11/2004 | WO | WO 02/080786 | | 10/2002 |
| EP | 1527747 A2 | 5/2005 | WO | WO02/080786 | | 10/2002 |
| EP | 1530952 A1 | 5/2005 | WO | WO 02/080793 | | 10/2002 |
| EP | 1532932 A1 | 5/2005 | WO | WO02/080793 | | 10/2002 |
| | | | WO | WO 02/080794 | | 10/2002 |

| | | |
|---|---|---|
| WO | WO02/080794 | 10/2002 |
| WO | WO 02/080795 | 10/2002 |
| WO | WO 02/080796 | 10/2002 |
| WO | WO02/080797 | 10/2002 |
| WO | WO 02/080797 | 10/2002 |
| WO | WO 02/080798 | 10/2002 |
| WO | WO 02/080799 | 10/2002 |
| WO | WO02/081170 | 10/2002 |
| WO | WO 02/081170 | 10/2002 |
| WO | WO 03/090630 A3 | 11/2003 |
| WO | WO 03/101311 | 12/2003 |
| WO | WO 2004/032776 A1 | 4/2004 |
| WO | WO2004/032777 | 4/2004 |
| WO | WO 2004/032777 | 4/2004 |
| WO | WO 2004/052221 | 6/2004 |
| WO | WO 2004/073488 A2 | 9/2004 |
| WO | WO 2004/073490 | 9/2004 |
| WO | WO2004/073490 | 9/2004 |
| WO | WO2004/073753 | 9/2004 |
| WO | WO 2004/082495 | 9/2004 |
| WO | WO 2004/098383 | 11/2004 |
| WO | WO 2004/103156 | 12/2004 |
| WO | WO 2005/004734 A1 | 1/2005 |
| WO | WO2005/004735 | 1/2005 |
| WO | WO 2005/110264 | 11/2005 |

OTHER PUBLICATIONS

Int'l Search Report EP 06005185.1 dated Apr. 18, 2006.
Int'l Search Report EP 06008779.8 dated Jun. 13, 2006.
Int'l Search Report EP 1683496 dated Jun. 13, 2006.
Int'l Search Report EP 04013772 dated Apr. 1, 2005.
Int'l Search Report EP 05013895 dated Oct. 14, 2005.
Int'l Search Report EP 05017281 dated Nov.16, 2005.
Int'l Search Report EP 06006716 dated Aug. 4, 2006.
Int'l Search Report PCT/US01/11224 dated Nov. 13, 2001.
Int'l Search Report EP 06014461.5 dated Oct. 20, 2006.
Int'l Search Report EP 06020584.6 dated Jan. 12, 2007.
Int'l Search Report EP 06020583.8 dated Jan. 30, 2007.
Int'l Search Report EP 06020756.0 dated Feb. 5, 2007.
Int'l Search Report EP 06024123.9 dated Fab. 26, 2007.
Int'l Search Report EP 06 020574.7 dated Sep. 21, 2007.
Int'l Search Report EP 07 010672.9 dated Oct. 1, 2007.
Int'l Search Report EP 07 013779.9 dated Oct. 18, 2007.
Int'l Search Report EP 07 009026.1 dated Sep. 12, 2007.
Int'l Search Report EP 07 015601.3 dated Dec. 6, 2007.
Int'l Search Report EP 07 015191.5 dated Dec. 19, 2007.
Int'l Search Report EP 07 020283.3 dated Jan. 16, 2008.
Sigel et al. "The Mechanism of Blood Vessel Closure by High Frequency Electrocoagulation" Surgery Gynecology & Obstetrics, Oct. 1965 pp. 823-831.
Bergdahl et al. "Studies on Coagulation and the Development of an Automatic Computerized Bipolar Coagulator" J.Neurosurg, vol. 75, Jul. 1991, pp. 148-151.
Kennedy et al. "High-burst-strength, feedback-controlled bipolar vessel sealing" Surgical Endoscopy (1998) 12: 876-878.
Peterson et al. "Comparison of Healing Process Following Ligation with Sutures and Bipolar Vessel Sealing" Surgical Technology International (2001).
Linehan et al. "A Phase I Study of the LigaSure Vessel Sealing System in Hepatic Surgery" Section of HPB Surger, Washington University School of Medicine, St. Louis MO, Presented at AHPBA, Feb. 2001.
Johnson et al. "Evaluation of the LigaSure Vessel Sealing System in Hemorrhoidectormy" American College of Surgeons (ACs) Clinicla Congress Poster (2000).
Sayfan et al. "Sutureless Closed Hemorrhoidectomy: A New Technique" Annals of Surgery vol. 234 No. 1 Jul. 2001 pp. 21-24.
Heniford et al. "Initial Results with an Electrothermal Bipolar Vessel Sealer" Surgical Endoscopy (2000) 15:799-801.
Heniford et al. "Initial Research and Clinical Results with an Electrothermal Bipolar Vessel Sealer" Oct. 1999.

McLellan et al. "Vessel Sealing for Hemostasis During Pelvic Surgery" Int'l Federation of Gynecology and Obstetrics FIGO World Congress 2000, Washington, D.C.
Levy et al. "Use of a New Energy-based Vessel Ligation Device During Vaginal Hysterectomy" Int'l Federation of Gynecology and Obstetrics (FIGO) World Congress 1999.
Crawford et al. "Use of the LigaSure Vessel Sealing System in Urologic Cancer Surger" Grand Rounds in Urology 1999 vol. 1 Issue 4 pp. 10-17.
Rothenberg et al. "Use of the LigaSure Vessel Sealing System in Minimally Invasive Surgery in Children" Int'l Pediatric Endosurgery Group (IPEG) 2000.
Palazzo et al. "Randomized clinical trial of Ligasure versus open haemorrhoidectomy" British Journal of Surgery 2002, 89, 154-157.
"Innovations in Electrosurgery" Sales/Product Literature; Dec. 31, 2000.
LigaSure Vessel Sealing System, the Seal of Confidence in General, Gynecologic, Urologic, and Laparaoscopic Surgery Sales/Product Literature; Jan. 2004.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC 2003.
"Reducing Needlestick Injuries in the Operating Room" Sales/Product Literature 2001.
Chung et al., "Clinical Experience of Sutureless Closed Hemorrhoidectomy with LigaSure" Diseases of the Colon & Rectum vol. 46, No. 1 Jan. 2003.
Strasberg et al., "Use of a Bipolar Vessel-Sealing Device for Parenchymal Transaction During Liver Surgery" Journal of Gastrointestinal Surgery, vol. 6, No. 4, Jul./Aug. 2002 pp. 569-574.
Paul G. Horgan, "A Novel Technique for Parenchymal Division During Hepatectomy" The American Journal of Surgery, vol. 181, No. 3, Apr. 2001 pp. 236-237.
W. Scott Helton, "LigaSure Vessel Sealing System: Revolutionary Hemostasis Product for General Surgery" Sales/Product Literature 1999.
Michael Choti, "Abdominoperineal Resection with the LigaSure Vessel Sealing System and LigaSure Atlas 20 cm Open Instrument" Innovations That Work, Jun. 2003.
Craig Johnson, "Use of the LigaSure Vessel Sealing System in Bloodless Hemorrhoidectomy" Innovations That Work, Mar. 2000.
Muller et al., "Extended Left Hemicolectomy Using the LigaSure Vessel Sealing System" Innovations That Work, Sep. 1999.
Herman et al., "Laparoscopic Intestinal Resection With the LigaSure Vessel Sealing System: A Case Report" Innovations That Work, Feb. 2002.
Carus et al., "Initial Experience With the LigaSure Vessel Sealing System in Abdominal Surgery" Innovations That Work, Jun. 2002.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
Levy et al., "Update on Hysterectomy—New Technologies and Techniques" OBG Management, Feb. 2003.
Barbara Levy, "Use of a New Vessel Ligation Device During Vaginal Hysterectomy" FIGO 2000, Washington, D.C.
McLellan et al. "Vessel Sealing for Hemostasis During Gynecologic Surgery" Sales/Product Literature 1999.
Sengupta et al., "Use of a Computer-Controlled Bipolar Diathermy System in Radical Prostatectomies and Other Open Urological Surgery" ANZ Journal of Surgery (2001) 71.9 pp. 538-540.
Olsson et al. "Radical Cystectomy in Females" Current Surgical Techniques in Urology, vol. 14, Issue 3, 2001.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
E. David Crawford "Evaluation of a New Vessel Sealing Device in Urologic Cancer Surgery" Sales/Product Literature 2000.
Joseph Ortenberg "LigaSure System Used in Laparoscopic 1st and 2nd Stage Orchiopexy" Innovations That Work, Nov. 2002.

Koyle et al., "Laparoscopic Palomo Varicocele Ligation in Children and Adolescents" Pediatric Endosurgery & Innovative Techniques, vol. 6, No. 1, 2002.
Dulemba et al. "Use of a Bipolar Electrothermal Vessel Sealer in Laparoscopically Assisted Vaginal Hysterectomy" Sales/Product Literature; Jan. 2004.
Johnson et al. "Evaluation of a Bipolar electrothermal Vessel Sealing Device in Hemorrhoidectomy" Sales/Product Literature; Jan. 2004.
Int'l Search Report PCT/US98/18640 dated Dec. 17, 1998.
Int'l Search Report PCT/US98/23950 dated Dec. 29, 1998.
Int'l Search Report PCT/US99/24869 dated Feb. 3, 2000.
Int'l Search Report PCT/US01/11218 dated Aug. 3, 2001.
International Search Report PCT/US01/11224 dated Nov. 13, 2001.
Int'l Search Report PCT/US01/11340 dated Aug. 7, 2001.
Int'l Search Report PCT/US01/11420 dated Oct. 8, 2001.
Int'l Search Report PCT/US02/01890 dated Jul. 17, 2002.
Int'l Search Report PCT/US02/11100 dated Jul. 9, 2002.
Int'l Search Report PCT/USO4/03436 dated Oct. 5, 2004.
Int'l Search Report PCT/US04/13273 dated Nov. 22, 2004.
Int'l Search Report PCT/US04/15311 dated Nov. 18, 2004.
Int'l Search Report EP 98944778 dated Oct. 31, 2000.
Int'l Search Report EP 98958575.7 dated Sep. 20, 2002.
Int'l Search Report EP 04027314 dated Mar. 10, 2005.
Int'l Search Report EP 04027479 dated Mar. 8, 2005.
Int'l Search Report EP 04027705 dated Feb. 3, 2005.
Int'l Search Report EP 05013463.4 dated Sep. 28, 2005.
Int'l Search Report EP 05017281 dated Nov. 16, 2005.
Int'l Search Report EP 05019130.3 dated Oct. 18, 2005.
Int'l Search Report EP 05020665.5 dated Feb. 16, 2006.
Int'l Search Report EP 05020666.3 dated Feb. 17, 2006.
Int'l Search Report EP 05021779.3 dated Jan. 18, 2006.
Int'l Search Report EP 05021197.8 dated Jan. 31, 2006.
Int'l Search Report EP 05021937.7 dated Jan. 13, 2006.
Int'l Search Report—extended- EP 05021937.7 dated Mar. 6, 2006.
Int'l Search Report EP 05023017.6 dated Feb. 16, 2006.
Int'l Search Report EP 05021780.1 dated Feb. 9, 2006.
Int'l Search Report EP 06002279.5 dated Mar. 22, 2006.
Int'l Search Report EP 04 752343.6 dated Jul. 20, 2007.
Int'l Search Report EP 06 024122.1 dated Mar. 19, 2007.
Int'l Search Report EP 07 001480.8 dated Apr. 12, 2007.
Int'l Search Report EP 07 001488.1 dated May 29, 2007.
Int'l Search Report—Extended EP 07 009029.5 dated Jul. 12, 2007.
Int'l Search Report EP 07 009321.6 dated Aug. 17, 2007.

* cited by examiner

APPARATUS AND METHOD FOR ELECTRODE THERMOSURGERY

BACKGROUND

1. Technical Field

The present disclosure relates to an electrosurgical system and method. More particularly, the present disclosure relates to an apparatus and method for tissue ablation having increased electrode temperature control.

2. Background of Related Art

Therapeutic lesions in living bodies have been accomplished for many decades using radio-frequency (RF) and other forms of energy. The procedures have been particularly useful in the field of neurosurgery, typically where RF ablation electrodes (usually of elongated cylindrical geometry) are inserted into a living body. A typical form of such ablation electrodes incorporates an insulated sheath from which an exposed (uninsulated) tip extends.

Generally, the ablation electrode is coupled between a grounded RF power source (outside the body) and a reference ground or indifferent electrode for contacting a large surface of the body. When an RF voltage is provided between the reference electrode and the inserted ablation electrode, RF current flows from the ablation electrode through the body. Typically, the current density is very high near the tip of the ablation electrode, which heats and destroys the adjacent tissue.

Ablation electrode techniques, including the theory behind the techniques and many applications of the techniques are described in various papers, specifically see, (1) Cosman et al, "Theoretical Aspects of Radiofrequency Lesions in the Dorsal Root Entry Zone" Neurosurg 15:945-950, 1984 and (2) Cosman E. R. and Cosman B. J.: "Methods of Making Nervous System Lesions, in Wilkins R H, Rengachary S S (EDS): Neurosurgery, New York, McGraw-Hill, Vol. III, pp. 2490-2498, 1984.

In the past, RF ablation electrodes have incorporated temperature sensors, for example, in the form of a thermistor or thermocouple. In that regard, see U.S. Pat. No. 4,411,266 (1983, Eric R. Cosman). Typically, the sensor is connected to a monitoring apparatus for indicating temperature to assist in accomplishing a desired lesion. As generally known, for a given tip geometry and tip temperature, lesions of a prescribed size can be made quite consistently. In that regard also, see U.S. Pat. No. 4,411,266, (1983, Eric R. Cosman).

Over the years, a wide variety of RF electrode shapes and configurations have been used, for example, several current forms are available from ValleyLab Inc., Boulder, Colo. Such electrodes have been used to accomplish lesions in a wide variety of targets within the body, including the brain, the spinal column and the heart.

However, a limitation of prior electrode ablation systems relates to the temperature of the tip. Specifically, prior ablation electrodes of a given tip geometry should not effectively exceed a temperature of 100.degree. C. At that temperature, the surrounding tissue will boil and char. Also, uncontrolled disruption, such as hemorrhage and explosive gas formation, may cause extremely hazardous and clinically dangerous effects on the patient. Consequently, the lesion size for a given electrode geometry generally has been considered to be somewhat limited by the fact that the tissue near the tip must not exceed 100.degree. C.

Essentially, during RF ablation, the electrode temperature is highest near the tip, because the current density is the highest at that location. Accordingly, temperature falls off as a function of distance from the electrode tip, and except for possible abnormalities in tissue conductivity, in a somewhat predictable and even calculable pattern. As an attendant consequence, the size of RF lesions for a given electrode geometry have been somewhat limited.

One proposed solution to the limitation of lesion's size has been to employ "off-axis" electrodes, for example the so called Zervas Hypophysectomy Electrode or the Gildenberg Side-Outlet electrode, as manufactured by Integra Radionics, Inc, Burlington, Mass. However, such systems in requiring multiple tissue punctures, increase the risk of hemorrhage, severely prolong the time of surgery and increase the level of delicacy. An umbrella of off-axis lesions may not produce a desired homogenous or uniform lesion.

SUMMARY

Accordingly, the present disclosure is directed to an electrosurgical instrument for use with a source of electrical energy to ablate tissue in a living subject. In one embodiment, the instrument includes an electrosurgical instrument for use with a source of electrical energy to ablate tissue in a living subject. The instrument includes an elongated tissue-penetrating electrode including a rigid tubular member with a closed distal end defining an interior cavity extending from the closed distal end to a proximal end of the rigid tubular member. The rigid tubular member defines an electrically conductive surface capable of receiving electrical energy from the source of electrical energy. The instrument also includes at least one electrically conductive segment located on the electrode, the segments configured to receive electrosurgical energy from the rigid tubular member. The instrument also includes an insulation layer disposed upon the elongated tissue-penetrating electrode defining an exposed portion of the electrode at the distal end and at least one sensor disposed which detects a temperature during ablation.

According to another embodiment of the present disclosure a system for targeting and ablating a predetermined volume of tissue to maximize the formation of a lesion is provided. The system includes an electrical energy generator and an elongated tissue-penetrating electrode including a rigid tubular member with a closed distal end defining an interior cavity extending from the closed distal end to a proximal end of the rigid tubular member. The rigid tubular member defines an electrically conductive surface capable of receiving electrical energy from the electrical energy generator. The system also includes at least one electrically conductive segment located on the electrode, the at least one electrically conductive segment configured to receive electrosurgical energy from the rigid tubular member.

An insulation layer is disposed upon the elongated tissue-penetrating electrode and defines an exposed portion of the electrode at the distal end. The instrument further includes at least one sensor disposed within the electrode or the at least one electrically conductive segment which detects a temperature and a fluid conduit sized to extend into the interior cavity of the rigid tubular member. The fluid conduit has a first end in fluid communication with an adjustable fluid source and a second end in fluid communication with the rigid tubular member. The adjustable fluid source adaptively provides coolant to the fluid conduit.

The present disclosure also relates to a method for targeting and ablating a volume of tissue to maximize the formation of a lesion. The method includes the step of providing an elongated tissue-penetrating electrode including a rigid tubular member with a closed distal end defining an interior cavity extending from the closed distal end to a proximal end of the rigid tubular member. The rigid tubular member defines an electrically conductive surface capable of receiving electrical energy from the source of electrical energy. The method also includes the step of placing at least one electrically conductive segment on the electrode, the at least one segment configured to receive electrosurgical energy from the rigid tubular member and disposing an insulation layer upon the elongated tissue-penetrating electrode defining an exposed portion of the electrode at the distal end. The method may further include the steps of detecting a temperature using at least one sensor disposed within the electrode or the at least one electrically conductive segment and supplying electrical energy from the generator to the rigid tubular member. The method also includes supplying coolant through a fluid conduit to the closed distal end of the rigid tubular member according to the detected temperature using an adjustable source of coolant and controlling a flow of electrical energy from the rigid tubular member to the at least one electrically conductive segment using one or more processors. The step of controlling a flow of coolant from the adjustable source of coolant to the distal end of the rigid tubular member using at least one processor may also be provided.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail. Those skilled in the art will understand that the invention according to the present disclosure may be adapted for use with either monopolar or bipolar electrosurgical systems.

Figure 1:
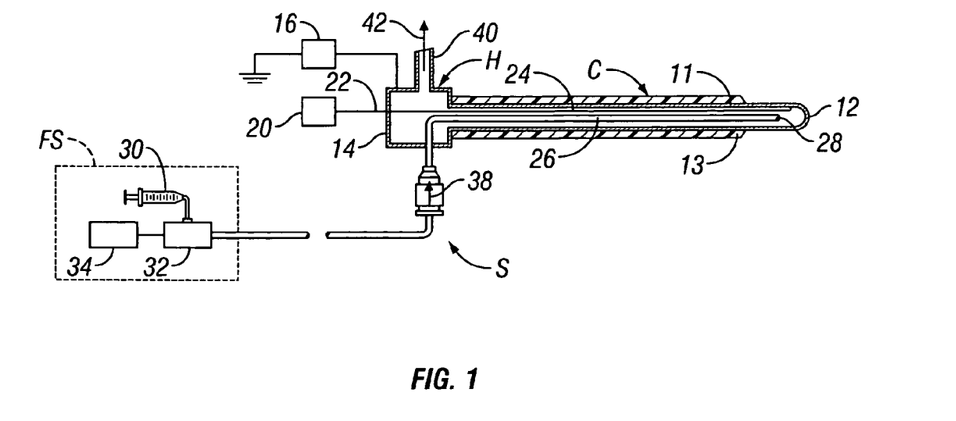
FIG. 1 is a block and sectional diagram of a system constructed in accordance with a prior art device.
Figure 2:
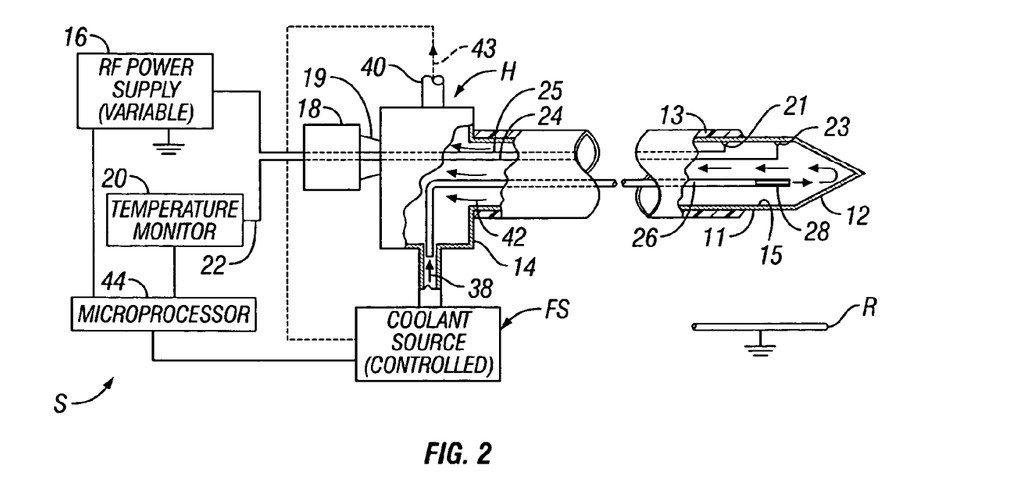
FIG. 2 is an enlarged block and sectional diagram of the prior art illustrating portions of the system of FIG. 1 in greater structural detail and with slight modifications.

Referring concurrently to FIGS. 1 and 2, the illustrated ablation system generally incorporates an elongated shaft or cannula body C for insertion, either percutaneously or intraoperatively into an open wound site. As illustrated, the cannula body C is integral with a head or hub element H coupled to remote support components, collectively designated S.

Structurally, cannula body C incorporates an elongated ablative electrode 11 (FIG. 2) formed of conductive material, e.g. metal such as stainless steel, titanium, etc. At the distal end of the cannula body C, electrode 11 defines a tip 12 that may be radiused at its end or which may be pointed. In one form, tip 12 may define a trocar point and may be of robust metal construction to facilitate insertion or penetration of tissue. In operation, when using an R.F. power supply 16, electrical current spreads from tip 12 to pass through the surrounding tissue causing the tissue to heat up. That is, when tip 12 is positioned contiguous (near, touching or within) to tissue, energy from R.F. power supply 16 is dissipated into heat within the tissue.

Over most of its length, electrode 11 carries an insulative coating 13 for selectively preventing the flow of electrical current from shaft 15 of electrode 11 into surrounding tissue. Thus, insulative coating 13 shields the intervening tissue from RF current, so that such tissue is not substantially heated along the length of shaft 15 except by the heating effect from exposed tip 12. Insulative material 13 may be constructed from a variety of different materials, including, but not limited to, ceramics, glass and polymeric materials.

The proximal end of electrode 11 (FIG. 2) is integral with an enlarged housing 14 of hub H that carries electrical and coolant connections, as explained in greater detail below. Outside the patient's body, housing 14 may be of a cylindrical configuration, defining ports for connections to the support components S, i.e., electrical and fluid couplings. As suggested, housing 14 may be integral with electrode 11, formed of metal, or it may constitute a separate subassembly as described below. Alternatively, housing 14 can be of plastic, accommodating separate electrical connections. In that regard, a plastic housing 14 is amenable to low artifact imaging by X-rays, CT, MRI, etc. as may be desirable in some situations.

Housing 14 mates with a block 18 (FIG. 2) defining a luer taper lock 19, essentially sealing block 18 to housing 14. Thus, fluid and electrical couplings are provided. Specifically, connection to a regulated RF supply 16 (variable) can take the form of a standard cable connector, a leader wire, a jack-type contact or other designs known in the high frequency art. The temperature-sensing and radiofrequency electrical connections can be made through housing 14 and extend to the region of tip 12, where an RF line 25 is connected by junction 21 (a weld, braze, or other secure electrical connection). Sensor lines 24 extend to a thermo-sensor 23, as in the form of a thermistor, or a thermocouple, or other type of sensor. Thermo sensor 23 may be fused or in thermal contact with the wall of tip 12 to sense the temperature of tip 12.

RF power supply 16 may be referenced to reference potential as illustrated (FIG. 2), and coupled through block 18 affixed to hub H. Specifically, RF power supply 16 provides RF current through line 25, which extends through block 18 and on to connection junction 21 located on electrode 11. Power supply 16 may take the form of an RF generator as exemplified by the RFG-3C RF Lesion Generator System available from Valleylab, Inc., Boulder, Co.

As indicated above and in accordance with common practice, when ablation electrode 11 is in a patient's body, an electrical circuit is completed through the body to a reference or dispersive electrode R (symbolically represented in FIG. 2) that is connected elsewhere to the body. Consequently RF power supply 16 heats body tissue by sending current from tip 12. In that regard, a temperature monitor 20 (FIG. 2 left, center) may be electrically connected by line 22 to temperature sensor 23 as in the form of a thermocouple or thermistor typically within or contacting tip 12. As illustrated, sensor 23 is connected to tip 12. The sensed temperature may be utilized to control either or both the flow of RF energy or the flow of coolant to attain the desired ablation. Note that a plurality of sensors could be utilized including those that could extend outside tip 12 to measure temperatures existing at various locations in the proximity of tip 12. Temperature monitor 20 may be as exemplified by the TC thermocouple temperature monitoring devices available from Valleylab, Inc., Boulder, Co.

In accordance herewith, temperatures at or near tip 12 (manifest by monitor 20) may be controlled by controlling the flow of fluid coolant through ablation electrode 11. Accordingly, the temperature of the tissue contacting or near tip 12 is controlled. In the disclosed embodiment, fluid from a fluid source FS is carried the length of ablation electrode 11 (FIG. 2) through a tube 26 extending from housing H to the distal end of electrode 11 terminating in an open end 28 at tip 12. At the opposite end of electrode 11, within housing H, tube 26 is connected to receive fluid. As illustrated in the detailed structure of FIG. 1, fluid source FS includes a source unit 34 coupled through a control 32 utilizing a hypodermic syringe 30 to actuate fluid flow (arrow 38) through a coupling 38. Thus, fluid flow is regulated in accordance with observed temperature, allowing increased flow of RF energy.

The fluid coolant may take the form of water or saline for the convection removal of heat from tip 12. Reservoir or source unit 34 (FIG. 1) might be a large reservoir of cooled water, saline or other fluid. As a simplistic example, a tank of water with ice cubes can function to maintain the coolant at a temperature of approximately 0° C. As another example, the fluid source FS could incorporate a peristaltic pump or other fluid pump, or could merely be a gravity feed for supplying fluid from a bag or rigid tank.

Flow away from tip 12 (FIG. 2) exits hub H through an exit port 40, as illustrated by arrows 42 and 43. Note that the ports may take the form of simple couplings, rigid units or may comprise flexible tubular couplings to reduce torque transmission to the electrode 11. Also, the coolant flow members may take the form of PVC tubes with plastic luer connectors.

As a result of the coolant flow, the interior of electrode 11, in particular electrode tip 12, can be held to a temperature near that of the fluid source FS. The coolant can circulate in a closed system as illustrated in FIG. 2. Also, in some situations, it may be desirable to reverse the direction of fluid flow from that depicted in the figures. As treated in detail below, coordinated operation involving RF heating along with the cooling may be accomplished by a microprocessor 44 (FIG. 2). In that regard, microprocessor 44 is coupled to RF power supply 16, temperature monitor 20 and fluid source FS to receive data on flow rates and temperatures and exercise control. Accordingly, an integrated operation is provided with feedback from temperature monitor 20 in a controlled format and various functions can be concurrently accomplished. Thus, facilitated by the cooling, the temperature profile of ablation electrode 11 may be moderated, changed, controlled or stabilized. Such controlled operation can effectively reduce the temperature of tissue near tip 12 to accomplish an equilibrium temperature distribution tailored to the desired lesion size.

The temperature distribution in the tissue near tip 12 depends on the RF current from tip 12 and depends on the temperature of the tissue that is adjacent to tip 12 and that tip temperature can be controlled to approach the temperature of the fluid from the source FS. Thus, a thermal boundary condition may be established, holding the temperature of the tissue (near tip 12) to approximately the temperature of the tip itself, e.g. the temperature of the fluid inside tip 12. Accordingly, by temperature control, a surgeon may impose a defined temperature at the boundary of electrode tip 12, which can be somewhat independent of the RF heating process and, in fact, dramatically modify the temperature distribution in the tissue.

Heat is generated in the following manner during ablation. The area of the ablation electrode 11 that is in contact with the ablation site (i.e., the tip 12) affects the current density of the signal that heats the tissue. The smaller the contact area the ablation electrode 11 has with the tissue, the greater the current density and the greater and more concentrated the heating of tissue. Conversely, the greater the contact area of the ablation electrode 11, the smaller the current density and the less heating of tissue. Further, the greater the heating of tissue, the greater the probability of burning the tissue. It is therefore important to either ensure a relative high amount of contact area between the ablation electrode 11 and the tissue, or otherwise maintain a relatively low current density on the ablation electrode 11.

While there are various methods of maintaining a relatively low current density (including the use of electrosurgical return electrode monitors (REMs), such as the one described in commonly-owned U.S. Pat. No. 6,565,559, the entire contents of which are incorporated by reference herein), the present disclosure ensures ablation electrode 11 maintains a low current density by controlling the temperature created by the current over the surface of the ablation electrode 11.

Figure 3A:
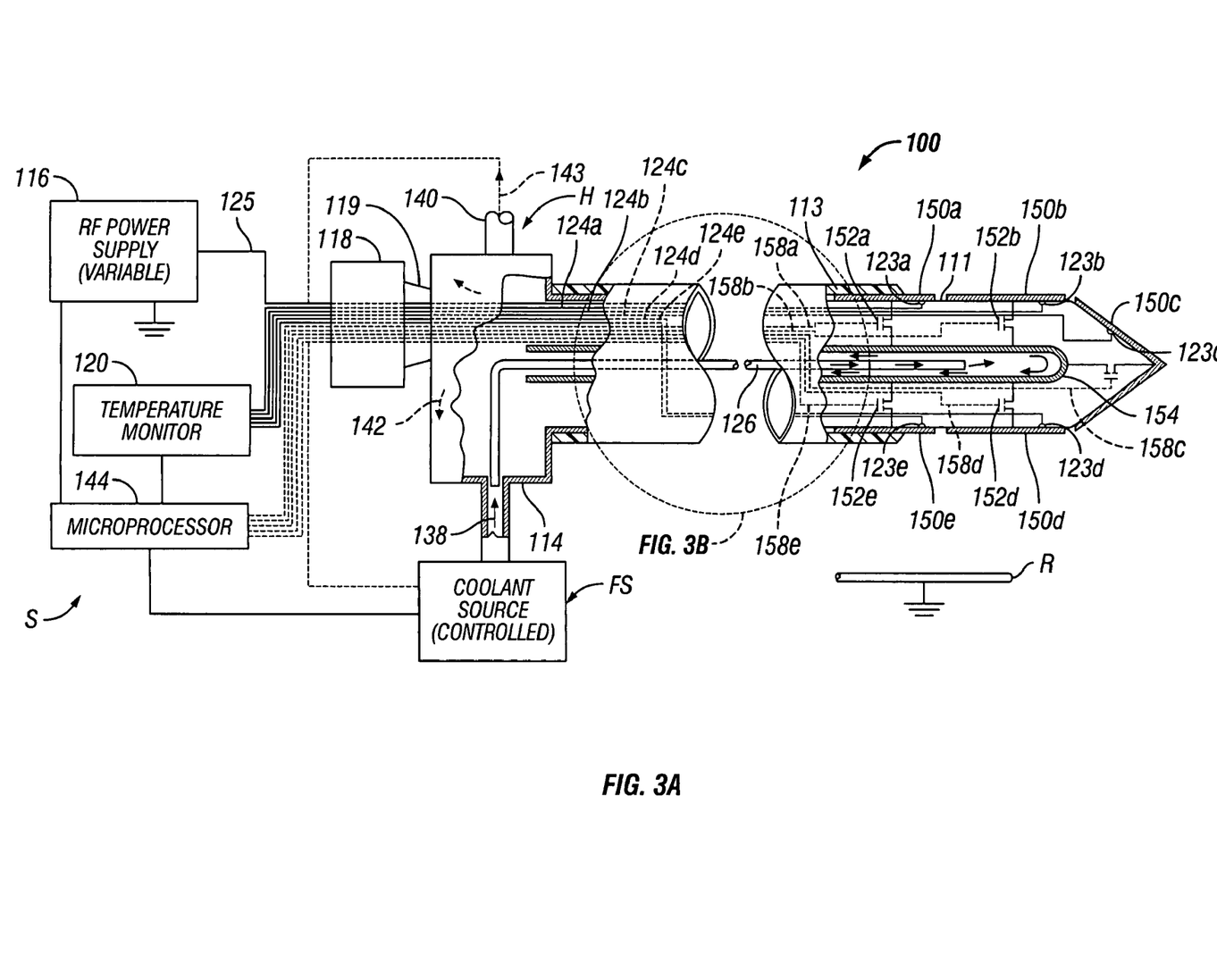
FIG. 3A is a greatly enlarged block and sectional diagram of the present disclosure showing a plurality of electrically conductive segments.
Figure 3B:
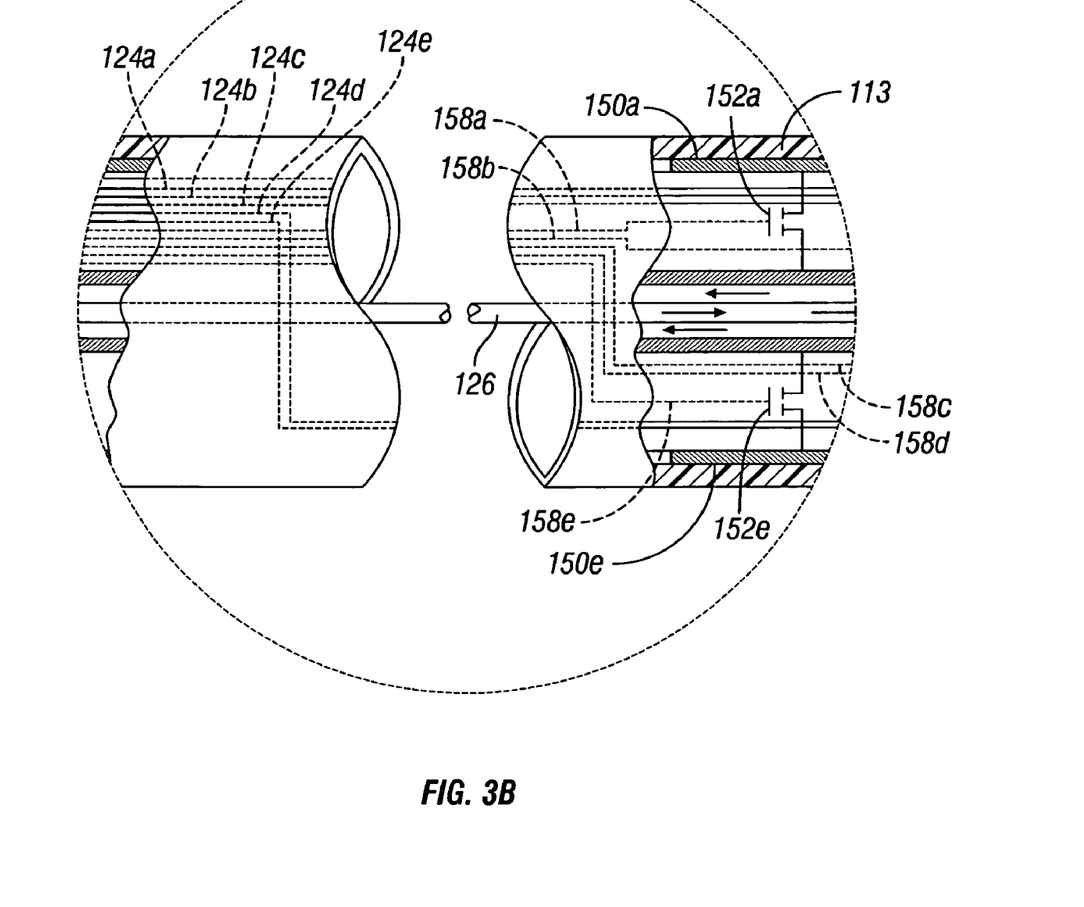
FIG. 3B is a view of the area of detail in FIG. 3A.

Referring now to FIGS. 3A and 3B, one embodiment of electrosurgical instrument 100 according to the present disclosure is shown for use with a source of electrical energy to ablate tissue in a living subject. Electrosurgical instrument 100 includes electrode 111 having a rigid tubular member 154 contained therein. Rigid tubular member 154 is electrically conductive and is operatively connected to RF power supply 116 as discussed in greater detail below. Electrically conductive segments 150a-e are disposed on the exterior surface of electrode 111. Segments 150a-e are configured to receive electrosurgical energy from the rigid tubular member 154 as also discussed in greater detail below. Electrode 111 also includes an insulation layer 113 disposed upon segments 150a-e and/or electrode 111. Insulation layer 113 defines an exposed portion of instrument 100, and may be constructed from a variety of suitable materials, such as those mentioned above.

Electrically conductive segments 150a-e are each connected to rigid tubular member 154 by respective transistors 152a-e. The gate of each transistor 152a-e is connected to a respective control line 158a-e, which leads to a microprocessor 144 or control unit that controls the flow of electrical energy to segments 150a-e. In this arrangement, transistors 152a-e act as switches that provide control over the energy output profile delivered to respective segments 150a-e. Activation of any particular control line triggers current flow from rigid tubular member 154 to the selected segment 150 (e.g., activation of control line 158b allows current to flow from rigid tubular member 154, through transistor 152b to segment 152b). Microprocessor 144 may be housed within and may work in conjunction with an electrosurgical generator (not explicitly shown) to regulate and control the various transistors.

Rigid tubular member 154 may be coated with a suitable semiconductive material in order to create transistors 152a-e. Transistors 152a-e may be constructed from a variety of different designs, including, but not limited to, Metal Oxide Semiconductor Field Effect Transistors (MOSFETs). These may be created using techniques known in the semiconductor industry, such as those used in the construction of integrated circuits. For a more detailed explanation of MOSFETs and their construction see CMOS VLSI DESIGN: A CIRCUITS AND SYSTEMS PERSPECTIVE, by N. Weste et al., Pearson Education, Boston, Mass., 2005.

Rigid tubular member 154 includes a closed distal end and defines an interior cavity extending from the closed distal end to a proximal end of rigid tubular member 154. Tubular member 154 contains a fluid conduit or tube 126. Tube 126 is sized to extend into the interior cavity and is adapted to be connected to a source of coolant "FS" to supply coolant for cooling tissue. Coolant source "FS" may be an adjustable source of coolant for adaptively providing coolant to fluid conduit 126 according to the detected temperature. As mentioned above, coolant source "FS" may work in conjunction with microprocessor 144, RF power supply 116 and temperature monitor 120 to adjust coolant flow in order to achieve the desired temperature.

In FIG. 3, Temperature sensors 123a-e and corresponding temperature lines 124a-e are similar to those described herein above and shown in FIG. 2 as temperature sensor 23 and corresponding temperature line 24. However, sensors 123a-e provide the temperature status of respective segments 150a-e, therefore allowing for a more detailed temperature profile. Temperature lines 124a-e may be connected to temperature monitor 120, microprocessor 144 or both. Using the data obtained from temperature sensors 123a-e the levels of RF current and coolant may be adjusted to achieve the desired results and to optimize instrument performance.

Figure 4A:
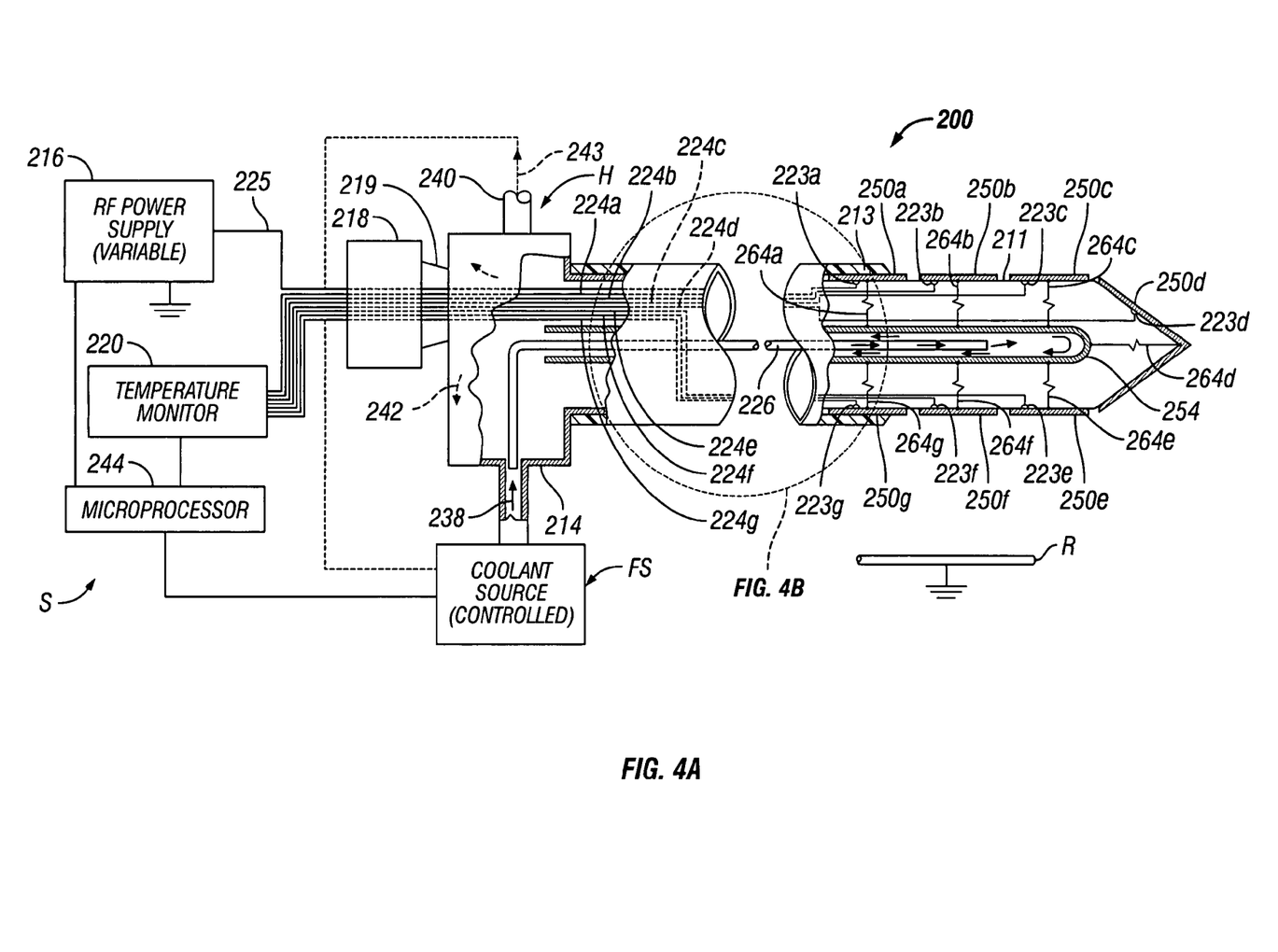
FIG. 4A is an enlarged block and sectional diagram of an alternate embodiment of the present disclosure showing a plurality of fixed resistors.
Figure 4B:
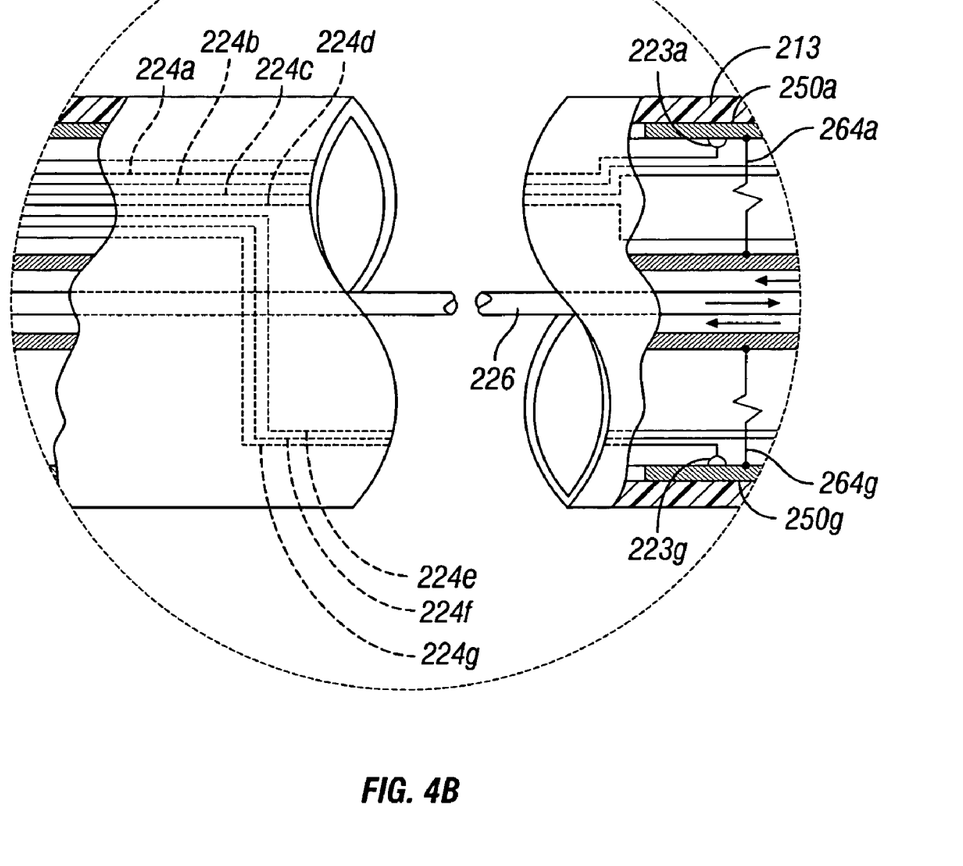
FIG. 4B is a view of the area of detail of FIG. 4A.

Referring now to FIGS. 4A-4B, an alternate embodiment of an electrosurgical instrument 200 according to the present disclosure is shown. FIG. 4 is similar to FIG. 3 above but replaces transistors 152 and corresponding control lines 156 with resistive layers 264a-g having a known fixed resistance. The fixed resistance values are selected so that a desired thermal profile is continuously provided. Using this configuration, instruments having numerous thermal geometries may be manufactured. Some of these thermal geometries may include, but are not limited to, spherical, cylindrical, conical, nonsymmetrical, polygonal etc.

Construction of fixed resistive layers is common in silicon wafer fabrication and similar techniques may be utilized here. Resistors are often built into integrated circuits as part of the fabrication process, using a semiconductor as the resistor. Electrode fabrication may utilize, inter alia, the following processes and devices: material deposition or removal processes, spin deposition, lithography, evaporators, ion beam etching and silicon beam etching.

RF power supply 216, temperature monitor 220, microprocessor 244 and coolant source "FS" all work in conjunction to produce a desired ablative effect. Instrument 200 works in a similar fashion to that described above in FIGS. 3A-3B but includes fixed resistors 264.

Figure 5:
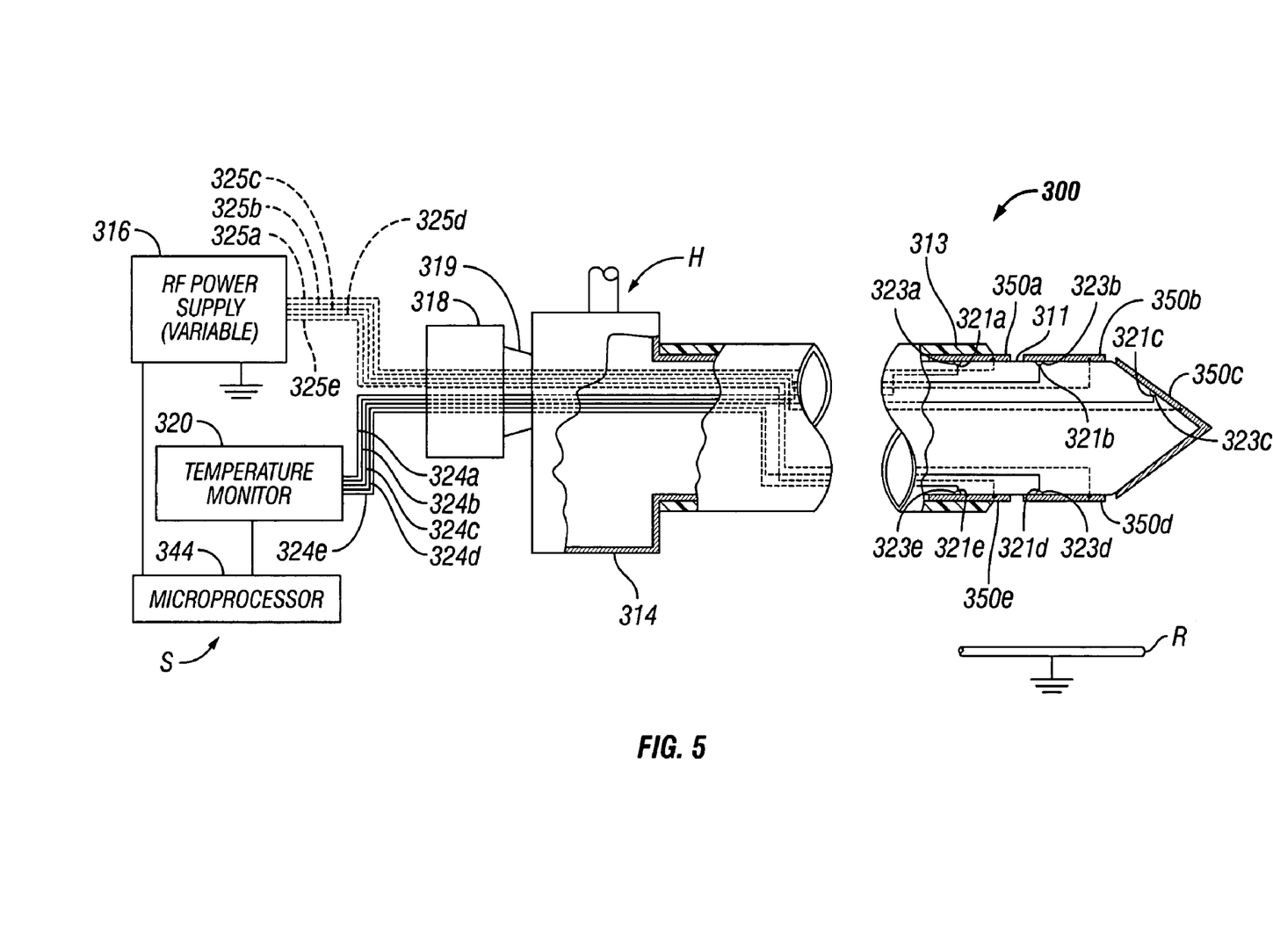
FIG. 5 is an enlarged block and sectional diagram of another embodiment of the present disclosure showing a plurality of electrically conductive segments having a direct connection with an electrical energy source.

FIG. 5 shows another embodiment of electrosurgical instrument 300 according to the present disclosure which includes rigid tubular member 154 of previous embodiments. In this embodiment, direct RF connections are made between RF Power Supply 316 and individual segments 350a-e. The amount of RF energy delivered to each segment 350a-e can be controlled using the microprocessor (which may be part of an electrosurgical generator (not shown)) to provide improved shaping of the thermal profile. Certain elements may utilize either monopolar or bipolar energy.

The present disclosure also relates to a method for targeting and ablating a volume of tissue to maximize the formation of a lesion. The method includes the step of providing an elongated tissue-penetrating electrode 111 including a rigid tubular member 154 with a closed distal end defining an interior cavity extending from the closed distal end to a proximal end of rigid tubular member 154. Rigid tubular member 154 defines an electrically conductive surface capable of receiving electrical energy from the source of electrical energy (such as an electrosurgical generator). The method also includes the step of placing at least one electrically conductive segment 150 on electrode 111. Segment 150 may be configured to receive electrosurgical energy from rigid tubular member 154. The method also includes the step of disposing an insulation layer 113 upon the elongated tissue-penetrating electrode 111, thereby defining an exposed portion of electrode 111 at the distal end. The method may also include the step of detecting the temperature of each electrically conductive segment 150 using a sensor 123 disposed upon each segment 150.

The method may further include the steps of supplying electrical energy (such as RF) from a generator or energy source to rigid tubular member 154 and supplying coolant through fluid conduit 126 to the closed distal end of rigid tubular member 154. The coolant flow may be selectively adjustable depending upon the measured temperature. The method may further include the step of controlling the flow of electrical energy from rigid tubular member 154 to each segment 150 using one or more microprocessors 144. Similarly, the method provides the step of controlling a flow of coolant from an adjustable source of coolant to the distal end of the rigid tubular member using one or more microprocessors 144. In certain embodiments, the step of activating a control line in order to allow electrical current to flow from rigid tubular member 154 to electrically conductive segment 154 may be included.

From the above description, it will be apparent to persons skilled in the art that the present invention may be embodied in a number of various forms. In that regard, the embodiment shown in the figures may be implemented variously, for example, to be either disposable or non-disposable. The thermal circulation system may or may not be an intact closed end, tissue-penetrating structure. Temperature sensors and monitors may or may not be used in the electrode or applicator.

Various forms of plastics, metals and composite materials may be utilized to accomplish specific objectives. For example, insulation coating 13 may take the form of Teflon, polyethylene, and the like. Numerous alternative embodiments of the present disclosure are envisioned.

Various energy sources could be employed as alternatives to RF energy. As examples, the energy could take the form of microwave energy, an ultrasonic heater providing sonic waves into tissue or a direct power source. Also as indicated, heating could be directed by various shapes of structures or variously apertured structures.

Alternative electrodes may take the form of a cannula with fiber optic channels to transmit laser light into the tissue for the generation of heat at a depth. Various geometries (curved or straight) of laser systems may be employed as well. One form of RF power supply may comprise the RFG-3C Lesion Generator as produced by Valleylab, Inc., Boulder, Colo., however, other suitable electrical power sources such as electrosurgical RF power supplies, bipolar cautery supplies, etc. could be utilized as well.

Various graphics displays may be incorporated in accordance herewith along with the cooling system as disclosed. Various controls may be provided for the cooling system and the heating system coordinated by observed or displayed phenomena. Various forms of feedback control are well-known and may be utilized in the present disclosure. For a detailed description of modern feedback control systems see FEEDBACK CONTROL OF DYNAMIC SYSTEMS, by G. Franklin et al., Prentice-Hall, Upper Saddle River, N.J., 2002.

As explained with respect to the disclosed embodiments, many variations of electrodes or body terminals are practical including tubular shafts, square shafts, etc. Flat electrodes, area electrodes, multiple electrodes, arrays of electrodes, electrodes with side-outlet or side-issued-tips, electrodes with balloon tips, expandable tips or conformable tips can be considered within the system. Electrodes with steerable tips and electrode shafts that can be conformed or shaped or that can be malleable can be considered within the system. Electrodes that are designed to be placed within the body tissue or on the surface of the body or within cavities within the bodies can be devised, which are encompassed herewith. Electrodes may or may not have temperature sensors within them or near them and, for instance, the ablation process can be done by supplying heating power and applicator cooling without temperature monitoring or control but merely using empirical parameters, such as heating power and cooling fluid temperature/flow.

While several embodiments of the disclosure are shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method for targeting and ablating a volume of tissue to maximize the formation of a lesion, the method comprising:
   providing an elongated tissue-penetrating electrode including a rigid tubular member and having at least one electrically conductive segment disposed on the electrode;
   directly coating a semiconductive material on the rigid tubular member, the semiconductive material forming at least one transistor, the at least one transistor configured to selectively connect the rigid tubular member with the at least one electrically conductive segment;
   detecting a temperature using at least one sensor during ablation;
   supplying electrical energy from a generator to the rigid tubular member;
   supplying coolant to the rigid tubular member according to the detected temperature using an adjustable source of coolant;
   controlling a flow of electrical energy from the rigid tubular member to the at least one electrically conductive segment; and
   controlling a flow of coolant from the adjustable source of coolant to the rigid tubular member.

2. The method according to claim 1, further comprising the step of connecting the rigid tubular member with the at least one electrically conductive segment through the at least one transistor.

3. The method according to claim 1, further comprising the step of attaching at least one control line to the at least one transistor.

4. The method according to claim 3, further comprising the step of activating the at least one control line in order to allow electrical current to flow from the rigid tubular member to the at least one electrically conductive segment.

5. The method according to claim 1, further comprising the step of providing at least one resistive layer configured to connect the at least one electrically conductive segment with the rigid tubular member.

6. An electrosurgical instrument for use with a source of electrical energy to ablate tissue in a living subject, the instrument comprising:
   an elongated tissue-penetrating electrode including a rigid tubular member having a closed distal end defining an interior cavity extending from the closed distal end to a proximal end of the rigid tubular member, the rigid tubular member defining an electrically conductive surface capable of receiving electrical energy from the source of electrical energy;
   at least one electrically conductive segment located on the electrode, the segments configured to receive electrosurgical energy from the rigid tubular member;
   an insulation layer disposed on the elongated tissue-penetrating electrode defining an exposed portion of the electrode at the distal end;
   at least one sensor that detects temperature of tissue during ablation; and
   a semiconductive material directly coated on the rigid tubular member and forming at least one transistor, the at least one transistor configured to selectively connect the rigid tubular member with the at least one electrically conductive segment.

7. The electrosurgical instrument according to claim 6, wherein the at least one transistor formed by the semiconductive material directly coated on the rigid tubular member is a field-effect transistor.

8. The electrosurgical instrument according to claim 6, further comprising at least one control line, the at least one control line configured to attach to the at least one transistor.

9. The electrosurgical instrument according to claim 8, wherein activation of a control line allows electrical current to flow from the rigid tubular member to an electrically conductive segment.

10. The electrosurgical instrument according to claim 6, further comprising at least one resistive layer configured to connect at least one electrically conductive segment with the rigid tubular member.

11. The electrosurgical instrument according to claim 10, wherein the resistive layer is constructed from a process selected from the group consisting of material deposition processes, removal processes, spin deposition, lithography, evaporators, ion beam etching and chemical etching.

12. The electrosurgical instrument according to claim 6, further comprising a fluid conduit sized to extend into the interior cavity of the rigid tubular member and adapted to be connected to a source of coolant to supply coolant for cooling tissue contiguous to the exposed portion of the electrode.

13. The electrosurgical instrument according to claim 2, wherein the source of coolant is an adjustable source of coolant for adaptively providing coolant to the fluid conduit according to the detected temperature.

14. A system for targeting and ablating a volume of tissue to maximize the formation of a lesion, the system comprising:
   an electrical energy generator;
   an elongated tissue-penetrating electrode including a rigid tubular member having a closed distal end defining an interior cavity extending from the closed distal end to a proximal end of the rigid tubular member, the rigid tubular member defining an electrically conductive surface capable of receiving electrical energy from the electrical energy generator;
   at least one electrically conductive segment located on the electrode, the at least one electrically conductive segment configured to receive electrosurgical energy from the rigid tubular member;
   a semiconductive material directly coated on the rigid tubular member and forming at least one transistor, the at least one transistor configured to selectively connect the rigid tubular member with the at least one electrically conductive segment;

an insulation layer disposed on the elongated tissue-penetrating electrode defining an exposed portion of the electrode at the distal end;

at least one sensor that detects a temperature during ablation; and a fluid conduit sized to extend into the interior cavity of the rigid tubular member, the fluid conduit having a first end in fluid communication with an adjustable fluid source, and a second end in fluid communication with the rigid tubular member, wherein the adjustable fluid source adaptively provides coolant to the fluid conduit.

15. The system according to claim 14, wherein the semiconductive material forms a plurality of transistors each connecting the rigid tubular member with one of the at least one electrically conductive segment.

16. The system according to claim 14, wherein the transistor formed on the rigid tubular member is a field-effect transistor.

17. The system according to claim 14, further comprising at least one control line, the at least one control line configured to connect the at least one transistor with a microprocessor.

18. The system according to claim 17, wherein activation of a control line allows electrical current to flow from the rigid tubular member to the at least one electrically conductive segment.

19. The system according to claim 14, further comprising at least one resistive layer configured to connect the at least one electrically conductive segment with the rigid tubular member.

20. The system according to claim 14, wherein the at least one electrically conductive segment is adapted to receive electrosurgical energy directly from the electrical energy generator.

* * * * *